US008628706B2

(12) United States Patent
Glenn, Jr. et al.

(10) Patent No.: US 8,628,706 B2
(45) Date of Patent: Jan. 14, 2014

(54) NON-LATHERING PERSONAL CARE COMPOSITION IN THE FORM OF AN ARTICLE

(75) Inventors: Robert Wayne Glenn, Jr., Liberty Township, OH (US); James Merle Heinrich, Fairfield, OH (US); Kathleen Mary Kaufman, Cincinnati, OH (US); Joanne Roberta Willman, fairfiled, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 0 days.

(21) Appl. No.: 13/597,539

(22) Filed: Aug. 29, 2012

(65) Prior Publication Data

US 2012/0321580 A1 Dec. 20, 2012

Related U.S. Application Data

(62) Division of application No. 12/424,812, filed on Apr. 16, 2009, now Pat. No. 8,273,333.

(60) Provisional application No. 61/045,444, filed on Apr. 16, 2008.

(51) Int. Cl.
*B29C 44/40* (2006.01)

(52) U.S. Cl.
USPC ............................ 264/50; 264/330; 424/400

(58) Field of Classification Search
USPC .......... 424/70.11, 70.12, 70.13, 70.19, 70.28, 424/70.31
See application file for complete search history.

(56) References Cited

U.S. PATENT DOCUMENTS

| 2,356,168 A | 8/1944 | Mabley |
|---|---|---|
| 2,396,278 A | 3/1946 | Lind |
| 2,438,091 A | 3/1948 | Lynch |
| 2,486,921 A | 11/1949 | Byerly |
| 2,486,922 A | 11/1949 | Strain |
| 2,528,378 A | 10/1950 | Mannheimer |
| 2,658,072 A | 11/1953 | Kosmin |
| 2,809,971 A | 10/1957 | Bernstein |
| 3,152,046 A | 10/1964 | Kapral |
| 3,236,733 A | 2/1966 | Karsten |
| 3,321,425 A | 5/1967 | Blau |
| 3,332,880 A | 7/1967 | Kessler |
| 3,426,440 A | 2/1969 | Shen |
| 3,489,688 A | 1/1970 | Pospischil |
| 3,653,383 A | 4/1972 | Wise |
| 3,695,989 A | 10/1972 | Albert |
| 3,753,196 A | 8/1973 | Kurtz |
| 3,761,418 A | 9/1973 | Parran, Jr. |
| 3,929,678 A | 12/1975 | Laughlin |
| 3,967,921 A | 7/1976 | Haberli |
| 4,020,156 A | 4/1977 | Murray |
| 4,051,081 A | 9/1977 | Jabs |
| 4,089,945 A | 5/1978 | Brinkman |
| 4,149,551 A | 4/1979 | Benjamin et al. |
| 4,196,190 A | 4/1980 | Gehman |
| 4,197,865 A | 4/1980 | Jacquet |
| 4,206,196 A | 6/1980 | Davis |
| 4,217,914 A | 8/1980 | Jacquet |
| 4,272,511 A | 6/1981 | Papantoniou |
| 4,323,683 A | 4/1982 | Bolich, Jr. |
| 4,345,080 A | 8/1982 | Bolich, Jr. |
| 4,379,753 A | 4/1983 | Bolich, Jr. |
| 4,381,919 A | 5/1983 | Jacquet |
| 4,422,853 A | 12/1983 | Jacquet |
| 4,470,982 A | 9/1984 | Winkler |
| 4,507,280 A | 3/1985 | Pohl |
| 4,529,586 A | 7/1985 | De Marco |
| 4,565,647 A | 1/1986 | Llenado |
| 4,663,158 A | 5/1987 | Wolfram |
| 4,710,374 A | 12/1987 | Grollier |
| 4,822,613 A | 4/1989 | Rodero |
| 4,885,107 A | 12/1989 | Wetzel |
| 4,976,953 A | 12/1990 | Orr |
| 4,990,280 A | 2/1991 | Thorengaard |
| 5,055,384 A | 10/1991 | Kuhnert |
| 5,061,481 A | 10/1991 | Suzuki |
| 5,062,889 A | 11/1991 | Hohl |
| 5,094,853 A | 3/1992 | Hagerty |
| 5,100,658 A | 3/1992 | Bolich, Jr. |
| 5,104,646 A | 4/1992 | Bolich, Jr. |
| 5,106,609 A | 4/1992 | Bolich, Jr. |
| 5,166,276 A | 11/1992 | Hayama |

(Continued)

FOREIGN PATENT DOCUMENTS

| CN | 1138091 A | 12/1996 |
|---|---|---|
| CN | 1219388 A | 6/1999 |

(Continued)

OTHER PUBLICATIONS

ISR dated May 6, 2011, PCT/US2009/067130, 5 pages.
ISR dated May 4, 2011, PCT/US2009/067088, 5 pages.
ISR dated Jul. 19, 2011, PCT/US2009/067088, 7 pages.
ISR dated May 9, 2011, PCT/US2009/067132, 5 pages.
ISR dated Jul. 20, 2011, PCT/US2009/067131, 5 pages.
ISR dated Apr. 29, 2011, PCT/US2009/067089, 5 pages.
ISR dated Jul. 15, 2009, PCT/IB2009/050388, 8 pages.
ISR dated Aug. 17, 2009, PCT/US2009/040739, 6 pages.
ISR dated Nov. 4, 2009, PCT/US2009/040739, 10 pages.
ISR dated Dec. 15, 2011, PCT/US2009/067087, 5 pages.

(Continued)

*Primary Examiner* — Vu A Nguyen
(74) *Attorney, Agent, or Firm* — Angela K. Haughey

(57) ABSTRACT

A non-lathering personal care article in the form of a porous dissolvable solid structure, comprising: from about 0% to about 10% ionic surfactant; from about 1% to about 60% of a non-surfactant cosmetic active; from about 15% to about 70% polymeric structurant, wherein the polymeric structurant has a weighted average molecular weight of from about 40,000 to about 500,000; and from about 1% to about 30% plasticizer. The article has a density of from about 0.03 g/cm3 to about 0.15 g/cm3.

3 Claims, No Drawings

(56) References Cited

U.S. PATENT DOCUMENTS

| | | |
|---|---|---|
| 5,220,033 A | 6/1993 | Kamei |
| 5,261,426 A | 11/1993 | Kellett et al. |
| 5,280,079 A | 1/1994 | Allen |
| RE34,584 E | 4/1994 | Grote |
| 5,391,368 A | 2/1995 | Gerstein |
| 5,409,703 A | 4/1995 | McAnalley |
| 5,429,628 A | 7/1995 | Trinh |
| 5,457,895 A | 10/1995 | Thompson |
| 5,476,597 A | 12/1995 | Sakata |
| 5,580,481 A | 12/1996 | Sakata |
| 5,582,786 A | 12/1996 | Brunskill |
| 5,660,845 A | 8/1997 | Trinh |
| 5,672,576 A | 9/1997 | Behrens |
| 5,674,478 A | 10/1997 | Dodd |
| 5,750,122 A | 5/1998 | Evans |
| 5,780,047 A | 7/1998 | Kamiya |
| 5,955,419 A | 9/1999 | Barket, Jr. |
| 5,976,454 A | 11/1999 | Sterzel et al. |
| 6,010,719 A | 1/2000 | Remon |
| 6,106,849 A | 8/2000 | Malkan |
| 6,177,391 B1 | 1/2001 | Zafar |
| 6,200,949 B1 | 3/2001 | Reijmer |
| 6,365,142 B1 | 4/2002 | Tamura |
| 6,458,754 B1 | 10/2002 | Velazquez |
| 6,503,521 B1 | 1/2003 | Atis |
| 6,525,034 B2 | 2/2003 | Dalrymple et al. |
| 6,790,814 B1 | 9/2004 | Marin |
| 6,800,295 B2 | 10/2004 | Fox |
| 6,831,046 B2 | 12/2004 | Carew et al. |
| 6,846,784 B2 | 1/2005 | Engel |
| 6,943,200 B1 | 9/2005 | Corrand |
| 7,015,181 B2 | 3/2006 | Lambino |
| 7,208,460 B2 | 4/2007 | Shefer et al. |
| 7,285,520 B2 | 10/2007 | Krzysik |
| 7,846,462 B2 | 12/2010 | Spadini et al. |
| 7,901,696 B2 | 3/2011 | Eknoian |
| 8,197,830 B2 | 6/2012 | Helfman et al. |
| 8,476,211 B2 | 7/2013 | Glenn, Jr. et al. |
| 2002/0064510 A1 | 5/2002 | Dalrymple |
| 2002/0077264 A1 | 6/2002 | Roberts |
| 2002/0081930 A1 | 6/2002 | Jackson |
| 2002/0098994 A1 | 7/2002 | Zafar |
| 2002/0099109 A1 | 7/2002 | Dufton |
| 2002/0177621 A1 | 11/2002 | Hanada |
| 2002/0187181 A1 | 12/2002 | Godbey |
| 2003/0032573 A1 | 2/2003 | Tanner |
| 2003/0045441 A1 | 3/2003 | Hsu |
| 2003/0069154 A1 | 4/2003 | Hsu |
| 2003/0080150 A1 | 5/2003 | Cowan |
| 2003/0099691 A1 | 5/2003 | Lydzinski |
| 2003/0099692 A1 | 5/2003 | Lydzinski |
| 2003/0180242 A1 | 9/2003 | Eccard |
| 2003/0186826 A1 | 10/2003 | Eccard |
| 2003/0194416 A1 | 10/2003 | Shefer |
| 2003/0199412 A1 | 10/2003 | Gupta |
| 2003/0207776 A1 | 11/2003 | Shefer |
| 2003/0209166 A1 | 11/2003 | Vanmaele et al. |
| 2003/0215522 A1 | 11/2003 | Johnson |
| 2003/0232183 A1 | 12/2003 | Dufton |
| 2004/0029762 A1 | 2/2004 | Hensley |
| 2004/0032859 A1 | 2/2004 | Mino |
| 2004/0048759 A1 | 3/2004 | Ribble |
| 2004/0053808 A1 | 3/2004 | Raehse |
| 2004/0071742 A1 | 4/2004 | Popplewell |
| 2004/0071755 A1 | 4/2004 | Fox |
| 2004/0108615 A1 | 6/2004 | Foley |
| 2004/0110656 A1 | 6/2004 | Casey |
| 2004/0126585 A1 | 7/2004 | Kerins |
| 2004/0175404 A1 | 9/2004 | Shefer |
| 2004/0202632 A1 | 10/2004 | Gott |
| 2004/0206270 A1 | 10/2004 | Vanmaele |
| 2004/0242097 A1 | 12/2004 | Hasenoehrl et al. |
| 2004/0242772 A1 | 12/2004 | Huth |
| 2005/0069575 A1 | 3/2005 | Fox |
| 2005/0136780 A1 | 6/2005 | Clark |
| 2005/0137272 A1 | 6/2005 | Gaserod |
| 2005/0202992 A1 | 9/2005 | Grandio Portabales |
| 2005/0232954 A1 | 10/2005 | Yoshinari |
| 2005/0272836 A1 | 12/2005 | Yaginuma |
| 2005/0287106 A1 | 12/2005 | Legendre |
| 2006/0002880 A1 | 1/2006 | Peffly |
| 2006/0013869 A1 | 1/2006 | Ignatious et al. |
| 2006/0052263 A1 | 3/2006 | Roreger |
| 2006/0228319 A1 | 10/2006 | Vona |
| 2007/0028939 A1 | 2/2007 | Mareri |
| 2007/0149435 A1 | 6/2007 | Koenig |
| 2007/0225388 A1 | 9/2007 | Cooper |
| 2008/0035174 A1 | 2/2008 | Aubrun-Sonneville |
| 2008/0083420 A1 | 4/2008 | Glenn et al. |
| 2008/0090939 A1 | 4/2008 | Netravali |
| 2008/0131695 A1 | 6/2008 | Aouad |
| 2008/0138492 A1 | 6/2008 | Cingotti |
| 2008/0152894 A1 | 6/2008 | Beihoffer |
| 2008/0215023 A1 | 9/2008 | Scavone |
| 2008/0293839 A1 | 11/2008 | Stobby |
| 2009/0232873 A1 | 9/2009 | Glenn, Jr. |
| 2010/0167971 A1 | 7/2010 | Glenn, Jr. |
| 2010/0173817 A1 | 7/2010 | Glenn, Jr. |
| 2010/0179083 A1 | 7/2010 | Glenn, Jr. |
| 2010/0279905 A1 | 11/2010 | Glenn, Jr. |
| 2010/0286011 A1 | 11/2010 | Glenn, Jr. |
| 2010/0291165 A1 | 11/2010 | Glenn, Jr. |
| 2010/0298188 A1 | 11/2010 | Glenn, Jr. |
| 2011/0023240 A1 | 2/2011 | Fossum |
| 2011/0028373 A1 | 2/2011 | Fossum |
| 2011/0028374 A1 | 2/2011 | Fossum |
| 2011/0182956 A1 | 7/2011 | Glenn, Jr. |
| 2011/0189246 A1 | 8/2011 | Glenn, Jr. |
| 2011/0189247 A1 | 8/2011 | Glenn, Jr. |
| 2011/0195098 A1 | 8/2011 | Glenn, Jr. |
| 2011/0250256 A1 | 10/2011 | Hyun-Oh et al. |
| 2012/0021026 A1 | 1/2012 | Chhabra |
| 2012/0270029 A1 | 10/2012 | Granberg et al. |
| 2012/0321580 A1 | 12/2012 | Glenn, Jr. et al. |

FOREIGN PATENT DOCUMENTS

| | | |
|---|---|---|
| CN | 1268558 A | 10/2000 |
| CN | 1357613 A | 7/2002 |
| CN | 1530431 A | 9/2004 |
| CN | 1583991 A | 2/2005 |
| DE | 19607851 A1 | 9/1997 |
| DE | 10331767 A1 | 2/2005 |
| EP | 609808 A1 | 8/1994 |
| EP | 0858828 A1 | 8/1998 |
| EP | 1160311 B1 | 12/2001 |
| EP | 1217987 B1 | 12/2004 |
| EP | 1958532 A2 | 8/2008 |
| EP | 2085434 A1 | 8/2009 |
| FR | 2871685 A | 12/2005 |
| FR | 2886845 A | 12/2006 |
| GB | 2235204 A | 2/1991 |
| GB | 2355008 A | 4/2001 |
| JP | 58021608 A | 2/1983 |
| JP | 58216109 A | 12/1983 |
| JP | 62-081432 | 4/1987 |
| JP | 62072609 A | 4/1987 |
| JP | 62072610 A | 4/1987 |
| JP | 1313418 A | 12/1989 |
| JP | 5344873 A | 12/1993 |
| JP | 6017083 A | 1/1994 |
| JP | 07-53349 | 2/1995 |
| JP | 7089852 A | 4/1995 |
| JP | 8325133 A | 12/1996 |
| JP | 10251371 A | 9/1998 |
| JP | 2003073700 A | 3/2003 |
| JP | 2003082397 A | 3/2003 |
| JP | 2004345983 A | 12/2004 |
| JP | 2005171063 A | 6/2005 |
| JP | 2007197540 A | 8/2007 |
| JP | 2007091954 A | 12/2007 |
| KR | 20020003442 | 1/2002 |
| WO | WO9514495 A1 | 6/1995 |
| WO | 01/19948 A1 | 3/2001 |

(56) References Cited

FOREIGN PATENT DOCUMENTS

| WO | 01/25322 A1 | 4/2001 |
|---|---|---|
| WO | 01/25393 A1 | 4/2001 |
| WO | WO01/24770 A1 | 4/2001 |
| WO | WO 01/25322 A1 * | 4/2001 |
| WO | 01/54667 A1 | 8/2001 |
| WO | WO 2004/032859 A | 4/2004 |
| WO | WO2004/041991 A1 | 5/2004 |
| WO | WO2005/003423 A1 | 1/2005 |
| WO | WO2007033598 A1 | 3/2007 |
| WO | WO2007/093558 A2 | 8/2007 |
| WO | WO2009019571 | 2/2009 |

OTHER PUBLICATIONS

ISR dated Jul. 19, 2011, PCT/US2009/067133, 4 pages.
ISR dated Jul. 19, 2011, PCT/US2009/067130, 7 pages.
ISR dated Apr. 27, 2011, PCT/US2010/059365, 5 pages.
ISR dated Apr. 27, 2011, PCT/US2010/059455, 5 pages.
ISR dated Apr. 27, 2011, PCT/US2010/059359, 5 pages.
T. Hildebrand, P. Rüegsegger. "Quantification of bone microarchitecture with the structure model index." Computer Methods in Biomechanics and Biomedical Engineering 1997; 1:15-23.
Vesterby, A.; Star volume in bone research. A histomorphometric analysis of trabecular bone structure using vertical sections; Anat Rec.; Feb. 1993; 235(2): 325-334.
C. D. Vaughan. Solubility, Effects in Product, Package, Penetration and Preservation, Cosmetics and Toiletries, vol. 103, Oct. 1988.
*Encyclopedia of Polymer Science and Engineering*, vol. 15, 2d ed., pp. 204-308, John Wiley & Sons, Inc. (1989).

Anonymous: "P8136 Poly(vinyl alcohol)" Internet article, [Online] XP002538935 Retrieved from the Internet: URL:http://www.sigmaaldrich.com/catalog/ProductDetail.do?D7=0&N25=SEARCH_CONCAT_PNO%7CBRAND_KEY&N4=P8136%7CSIAL&N25=0&QS=0N&F=SPEC> [retrieved on Jul. 28, 2009].
Office Action for U.S. Appl. No. 12/633,228 dated May 11, 2011; Glenn, Jr. et al.; filed Dec. 8, 2009.
Office Action for U.S. Appl. No. 12/633,228 dated Oct. 25, 2011; Glenn, Jr. et al.; filed Dec. 8, 2009.
Office Action for U.S. Appl. No. 12/633,257 dated Jun. 1, 2011; Glenn, Jr. et al.; filed Dec. 8, 2009.
Office Action for U.S. Appl. No. 12/633,257 dated Nov. 17, 2011; Glenn, Jr. et al.; filed Dec. 8, 2009.
Office Action for U.S. Appl. No. 12/633,301 dated Jun. 3, 2011; Glenn, Jr. et al.; filed Dec. 8, 2009.
Office Action for U.S. Appl. No. 12/633,301 dated Nov. 7, 2011; Glenn, Jr. et al.; filed Dec. 8, 2009.
Office Action for U.S. Appl. No. 12/633,550 dated Nov. 16, 2011; Glenn, Jr. et al.; filed Dec. 8, 2009.
Office Action for U.S. Appl. No. 12/633,335 dated Jul. 8, 2011; Glenn, Jr. et al.; filed Dec. 8, 2009.
Office Action for U.S. Appl. No. 12/633,415 dated Nov. 14, 2011; Glenn, Jr. et al.; filed Dec. 8, 2009.
Office Action for U.S. Appl. No. 12/633,572 dated Jul. 28, 2011; Glenn, Jr. et al.; filed Dec. 8, 2009.
Office Action for U.S. Appl. No. 12/361,634 dated Sep. 14, 2011; Glenn, Jr. et al.; filed Jan. 29, 2009.
U.S. Appl. No. 13/440,475, filed Apr. 5, 2012, Granberg et al.

* cited by examiner

NON-LATHERING PERSONAL CARE COMPOSITION IN THE FORM OF AN ARTICLE

CROSS REFERENCE TO RELATED APPLICATION

This application is a divisional of U.S. application Ser. No. 12/424,812, filed Apr. 16, 2009, which claims the benefit of U.S. Provisional Application No. 61/045,444, filed Apr. 16, 2008.

FIELD OF THE INVENTION

The present invention relates to non-lathering personal care compositions, especially those personal care compositions in the form of an article that is a porous, dissolvable solid structure.

BACKGROUND OF THE INVENTION

The majority of personal care products in the market today are sold as liquid products. While widely used, liquid products have disadvantages in terms of packaging, storage, transportation, and convenience of use.

Liquid personal care products typically are sold in bottles which add significant cost as well as packaging waste, much of which ends up in land-fills. Liquid personal care products also usually comprise a substantial amount of water in the formula which adds significant weight and size translating into greater shipping and storage costs. Liquid personal care products can also be difficult to use in terms of controlling dosage and the delivery of the product.

It is an object of the present invention to provide a non-lathering dissolvable solid personal care product that can be conveniently and quickly dissolved in the palm of the consumer to reconstitute a liquid product for ease of application to hair and/or skin while providing sufficient topical delivery of active agents for topical hair and/or skin applications. It is a further object of the present invention to provide such a product that can be produced in an economical manner via physical aeration followed by drying.

Existing dissolvable personal care films comprise a water-soluble polymeric structurant and active ingredients. However, in order to achieve the requisite rapid dissolution rates needed for consumer convenience, these films are generally on the order of less than 100 microns thickness (typically 50 microns) and, thereby, are generally of too low a basis weight (typically 50-100 grams of solid per square meter) to enable consumer application of a sufficient dosage of active ingredients for entire body or whole head hair application and performance, i.e., beyond lower dosage applications such as hand cleansing and/or the facial applications.

In order to achieve sufficient dosage of raw materials within the palm of the consumer for whole head hair and whole body skin applications, relatively high basis weights are needed which requires objects with a substantial third dimension (thickness) relative to thin films. Moreover, it has also been found that in order for these objects with a substantial third dimension to quickly dissolve in the palm of the consumer to reconstitute a liquid product for ease of application to hair/skin, they not only comprise a water-soluble polymeric structurant in combination with the active ingredients, but also are in the form of a highly porous and predominantly open-celled (vs. closed-celled) solid structure. It is believed that such water-soluble porous solids comprising predominantly open-cells enable rapid water flux inside the structure exposing a multiplicity of additional solid surface area for vastly increased dissolution rates. This is in contrast to water-soluble porous solids comprised of predominantly closed cells whereby the vast majority of the interior cellular surfaces are not rapidly exposed to the water upon wetting with dissolution progressing predominantly via surface erosion and resulting in slower dissolution.

The production of such rapidly dissolvable open-celled porous solid structures via physical aeration typically requires significant surfactancy as a production means to generate the initial wet foam that can then be dried to the porous solid. For cleansing applications, i.e., personal cleansing and hair shampoos, this is not a problem as this surfactancy is also congruent with the desired cleansing product performance (i.e., lathering). However, for non-cleansing applications, i.e., hair conditioning, styling, in-shower body lotions etc., this surfactancy may be problematic as it can adversely affect the deposition of the intended hydrophobic actives to the hair and skin as well as giving un-desirable in-usage signals of lathering/foaming/squeakiness to the consumer that is not congruent with the intended care functions of these products (conditioning, coating, depositing, moisturizing, styling etc.).

It is thus an object of the present invention to discover a means of production of the porous solids via physical aeration (foaming), and also enabling the formation of a predominantly open-celled foam for rapid dissolution, with minimal surfactancy such that the resulting rapidly dissolving porous solid is substantially non-lathering.

Freeze-drying aqueous solutions of water soluble polymeric structurants with other actives is a known method of producing rapidly dispersing or dissolving porous solids with predominantly open cells via sublimation of water from the aqueous mixture leaving behind a skeleton of the dried polymeric structurant. However, freeze-dried porous solids are typically void of plasticizing agents making them rigid and less desirable. Moreover, freeze-drying is an expensive process and less feasible for economical large scale production for personal care applications. Other traditional dissolvable personal care products include porous solids produced by an anhydrous extrusion process and employing volatile blowing agents to produce the cellular structure via high pressure drop induced expansion of the solid. However, this process is limited to anhydrous solid-sourced surfactants and ingredients which are limited in number and make it more difficult to formulate a personal care product with desired characteristics and performance. It would be highly desirable to produce substantially non-lathering and rapid dissolving porous solids with predominantly open-cells via physical aeration (high shear mechanical stirring or gas injection) and subsequent drying as a more commercially viable production method relative to freeze-drying. However, physical aeration essentially results in an air-in-water high internal phase emulsion (a closed cell wet foam) which upon drying can lead to dried closed cell foam morphology wherein the air bubbles are trapped/encased within the dried polymeric film lamellae or generally collapses into a film in the instances where the foam is unstable.

It is therefore an object of the present invention to provide a substantially non-lathering dissolvable open-celled porous solid personal care product that can be conveniently and quickly dissolved in the palm of the consumer to reconstitute a liquid product for ease of application to hair/skin while providing sufficient topical delivery of active agents for whole head hair and whole body skin applications (with similar performance as today's liquid products). It is a further object of the present invention to provide such a product that can be produced by physical aeration followed by subsequent drying. It is an even further object of the present invention to provide such a product with desirable softness and flexibility.

SUMMARY OF THE INVENTION

A substantially non-lathering personal care article in the form of a porous dissolvable solid structure, comprising from about 0% to about 10% ionic surfactant; from about 1% to about 60% of a non-surfactant cosmetic active; from about 15% to about 70% polymeric structurant, wherein the polymeric structurant has a weighted average molecular weight of from about 40,000 to about 500,000; and from about 1% to about 30% plasticizer; wherein the article has a density of from about 0.03 g/cm3 to about 0.15 g/cm3.

A pre-mix suitable for use in making a non-lathering personal care article that is in the form of a porous dissolvable solid structure, wherein said pre-mix has from about 15% to about 40% solids, has a viscosity of from about 2,500 cps to about 30,000 cps, and comprises (i) from about 0% to about 4% ionic surfactant; (ii) from about 0.3% to about 20% of a non-surfactant cosmetic active; (iii) from about 5% to about 25% polymeric structurant, and wherein the polymeric structurant has a weighted average molecular weight of from about 40,000 to about 500,000; and from about 0.3% to about 10% plasticizer.

A process for forming a non-lathering personal care article in the form of a porous dissolvable solid structure, wherein said process comprises the steps of: preparing a pre-mix comprising surfactant, dissolved polymer structurant, and optionally plasticizer, wherein said pre-mix has: from about 15% to 40% total solids; and a viscosity of from about 2,500 cps to 30,000 cps; aerating said pre-mix by introducing a gas into the pre-mix to form a wet aerated pre-mix; forming the wet aerated pre-mix into a desired one or more shapes to form shaped wet pre-mix; and drying the shaped wet pre-mix to a desired final moisture content, wherein the moisture content is from about 0.1% to about 15% moisture, to form the personal care article.

DETAILED DESCRIPTION OF THE INVENTION

In all embodiments of the present invention, all percentages are by weight of the total composition, unless specifically stated otherwise. All ratios are weight ratios, unless specifically stated otherwise. All ranges are inclusive and combinable. The number of significant digits conveys neither a limitation on the indicated amounts nor on the accuracy of the measurements. All numerical amounts are understood to be modified by the word "about" unless otherwise specifically indicated. Unless otherwise indicated, all measurements are understood to be made at 25° C. and at ambient conditions, where "ambient conditions" means conditions under about one atmosphere of pressure and at about 50% relative humidity. All such weights as they pertain to listed ingredients are based on the active level and do not include carriers or by-products that may be included in commercially available materials, unless otherwise specified.

Definitions

The term "porous solid" as used herein, unless otherwise specified, refers to a solid, interconnected, polymer-containing matrix that defines a network of spaces or cells that contain a gas, typically a gas such as air. The present invention describes personal care compositions in the form of open-celled porous dissolvable solid structures wherein the spaces or cells are substantially interconnected.

As used herein, the terms "substantially non-lathering" and "non-lathering" are used interchangeably throughout to mean a lather volume of from 0 ml to 20 ml.

"Personal care composition," as used herein, means a composition that may be applied to mammalian keratinous tissue without undue undesirable effects.

"Keratinous tissue," as used herein, means keratin-containing layers disposed as the outermost protective covering of mammals and includes, but is not limited to, skin, hair, scalp and nails.

The term "non-surfactant cosmetic active" or "cosmetic active" as used herein, means one or a mixture of more than one non-surfactant material(s) that, when applied to mammalian keratinous tissue, provide a benefit to the keratinous tissue. As used herein, the terms "non-surfactant cosmetic active" and "cosmetic active" are used interchangeably. The term "non-surfactant cosmetic active" is broad enough to include skin care actives, hair care actives, and beauty benefit agents, and may be used interchangeably with such terms throughout the present application. Cosmetic actives may deliver beauty benefits such as, but not limited to, sebum inhibition, altering the appearance of skin and/or hair, reducing dryness, itchiness and/or flakiness, reducing skin pore size, exfoliation, desquamation, improving the appearance of the keratinous tissue, conditioning, moisturizing, smoothening, etc.

"Beauty benefit" or "benefit", as used herein in reference to mammalian keratinous tissue includes, but is not limited to cleansing, sebum inhibition, altering the appearance of skin and/or hair, reducing dryness, itchiness and/or flakiness, reducing skin pore size, exfoliation, desquamation, improving the appearance of the keratinous tissue, conditioning, moisturizing, smoothening, etc.

The present inventors have found that dissolvable solid personal care products can be prepared that can be conveniently and quickly dissolved in the palm of the consumer to reconstitute a liquid product for ease of application to hair and/or skin while providing sufficient topical delivery of active agents for whole head hair and whole body skin applications (with similar performance as conventional liquid products). It has also been found that such products can be produced in an economical manner by physical aeration followed by subsequent drying. Additionally, it has been found that such products can now be produced with desirable softness and flexibility and to be substantially non-lathering.

To meet the above mentioned objects of the present invention, it has been found that a flexible personal care article in the form of a porous dissolvable solid structure can be made comprising ionic surfactant (from about 0% to about 10% anionic surfactant, in one embodiment from about 0% to about 6%, and in another embodiment from about 0% to about 3%); a non-surfactant cosmetic active (from about 1% to about 60% cosmetic active, in one embodiment from about 5% to about 50%, and in another embodiment from about 10% to about 40%); a polymer structurant comprising one or more water-soluble polymers (from about 15% to about 70 wt % polymer structurant, in one embodiment from about 22.5% to about 60%, and in a another embodiment from about 30% to about 50%); and a plasticizer (from about 1% to about 30% plasticizer, in one embodiment from about 3% to about 24%, and in another embodiment from about 5% to about 20%); and wherein the porous dissolvable solid structure has a density of from about 0.03 g/cm$^3$ to about 0.15 g/cm$^3$, in one embodiment from about 0.04 g/cm$^3$ to about 0.12 g/cm$^3$, and in an alternate embodiment from about 0.06 g/cm$^3$ to about 0.10 g/cm$^3$.

In another embodiment, the personal care article has a basis weight of from about 125 grams/m² to about 1,000 grams/m², in another embodiment from about 150 grams/m² to about 800 grams/m², in an alternate embodiment from about 200 grams/m² to about 700 grams/m², and in still another embodiment from about 300 grams/m² to about 650 grams/m²; and a thickness as defined herein of from about 0.5 mm to about 10 mm, in one embodiment from about 1 mm to about 7 mm, and in an alternate embodiment from about 2 mm to about 6 mm. In a further embodiment, the personal care article is produced by the process comprising the steps of preparing a pre-mix comprising surfactant, dissolved polymer structurant, and optionally plasticizer, wherein said pre-mix has: from about 15% to 40% total solids; and a viscosity of from about 2,500 cps to 30,000 cps; and aerating said pre-mix by introducing a gas into the pre-mix to form a wet aerated pre-mix; and then forming the wet aerated pre-mix into a desired one or more shapes to form shaped wet pre-mix; and then drying the shaped wet pre-mix to a desired final moisture content, wherein the moisture content is from about 0.1% to about 15% moisture, to form the personal care article.

According to yet another embodiment of the present invention, the polymer structurant comprises one or more water-soluble polymers wherein at least one of the polymers has a weighted average molecular weight of from about 40,000 to about 500,000, in another embodiment from about 50,000 to about 400,000, in an alternate embodiment from about 60,000 to about 300,000, and in still another embodiment from about 70,000 to about 200,000.

In a particular embodiment, at least one of the one or more water-soluble polymers is chosen such that a 2% by weight aqueous solution of the water-soluble polymer gives a viscosity at 20° C. of from about 4 centipoise to about 80 centipoise; in an alternate embodiment from about 5 centipoise to about 70 centipoise; and in another embodiment from about 6 centipoise to about 60 centipoise.

In a another embodiment, the flexible personal care article in the form of a porous dissolvable solid structure, comprises in one embodiment from about 1% to about 50% of a nonionic surfactant, and in another embodiment from about 5% to about 45% nonionic surfactant, and in another embodiment from about 10% to about 40% nonionic surfactant.

In another embodiment, the flexible personal care article in the form of a porous dissolvable solid structure, comprises from about 1% to about 50% of a polymeric surfactant, in another embodiment from about 5% to about 45% polymeric surfactant, and in yet another embodiment from about 10% to about 40% polymeric surfactant surfactant.

In the present invention the substantially non-lathering rapidly dissolving porous solids with a predominantly interconnected, open-celled structure can be produced via physical aeration followed by subsequent drying (as an alternative to conventional freeze drying). This can be accomplished by generating a physically aerated wet foam with a controlled degree of foam instability during the drying process such that the thin film bubble facings drain into the plateau borders concurrent to drying/solidification resulting in a plurality of open channels ("holes" and "struts") and, particularly, without collapse of the foam structure during the drying process thereby maintaining the physical strength and cohesiveness of the solid. Furthermore, it has been found that this instability and coalescence could be controllably manipulated such that the original closed-cell wet foam transforms within the multi-hour drying process into a true open-celled porous structure wherein the plurality of open channels extends to the solid's surface. Historically, when attempting to generate such products, the results were stable wet foams drying to conventional closed-cell solid foams or unstable wet foams drying to collapsed films. It was also surprising and non-intuitive to discover that the aeration to the initial wet foam prior to drying (a lathering process) can surprisingly be achieved in such a manner to produce the requisite open-celled porous structure, but with the resulting rapidly dissolving article being substantially non-lathering during consumer usage. This phenomenon has been achieved by employing special surfactants and surfactant combinations that enable lathering (foam generation) under the high energy processing conditions employed during aeration to produce the structure, but which are substantially non-lathering (little to no foam generation) under the lower energy consumer usage conditions when the solids undergo dissolution. It has been discovered that these two competing performance requirements can be achieved by (i) minimizing the presence of ionic surfactants, (ii) maximizing the presence of non-ionic surfactants and/or polymeric surfactants, (iii) minimizing the overall surfactant levels required for the aeration process, and (iv) combinations thereof.

It has been discovered that such substantially non-lathering open-celled dissolvable porous solids prepared by physical aeration followed by drying can only be achieved within a narrowly defined rheological range as defined above. Achieving the relatively low viscosity range required is problematic due to the typically high polymeric structurant levels required for solid integrity and cohesiveness as well as the desire for minimal water content (to minimize drying times and energy required for production). To achieve the required relatively low viscosity range of the present invention while producing integral and cohesive solid structures, it has been discovered that several compositional strategies can be employed, either alone or in combination, including but not limited to: (i) employing water-soluble polymers within the requisite molecular weight range but with relatively low viscosity build as defined herein; (ii) dilution of the processing mixture with water; (iii) adding electrolyte or hydrotrope to manipulate the viscosity; (iv) adding non-ionic surfactants which achieve a rheology thinning effect, or (v) adding low molecular weight solvents to manipulate the viscosity. Importantly, aerating processing mixtures below the required viscosity range results in less desirable, non-cohesive porous solids.

It has also been found that the above described characteristics of the present invention can be delivered by the production of open-celled porous structures employing either semi-continuous or continuous aeration equipment from the food industry that are used in the manufacture of marshmallows and dehydrated marshmallows.

I. COMPOSITION

Non-Surfactant Cosmetic Actives

The dissolvable personal care articles of the present invention may include any suitable cosmetic active. Such actives can include, but are not limited to, conditioning agents for skin and hair, hair coloring agents, hair bleaching agents, hair styling agents, skin actives, perfumes, self-warming agents, anti-dandruff agents, hair dyes, shaving lotion actives, sunscreen actives, insect repellant actives, rash lotion actives, anti-acne actives, hair straightener actives, hair perming actives, anti-microbial actives, skin tanning actives, hair restorer actives, hair shine actives, skin make-up actives, and combinations thereof. Furthermore, the article can comprise agents for stimulating hair growth and/or promoting the appearance of fuller and/or thicker hair. Such materials can include, but are not limited to, minoxidil; cocktails of niacinamide, panthenol, and caffeine; and mixtures thereof.

A. Conditioning Agents

The dissolvable personal care solids of the present invention may comprise an active agent comprising one or more conditioning agents suitable for application to the hair. In a particular embodiment, the conditioning agents are selected from the group consisting of high melting point fatty compounds, silicones, amido amines, acids, low melting point oils, waxes, cationic polymers, and cationic surfactants. The high melting fatty compound is incorporated in such a way and in combination with the other ingredients to provide a gel matrix which is suitable for providing various conditioning benefits such as slippery and slick feel on wet hair, and softness, moisturized feel, and fly-away control on dry hair.

The high melting point fatty compound useful herein have a melting point of 25° C. or higher, and is selected from the group consisting of fatty alcohols, fatty acids, fatty alcohol derivatives, fatty acid derivatives, and mixtures thereof. Non-limiting examples of the high melting point compounds are found in International Cosmetic Ingredient Dictionary, Fifth Edition, 1993, and CTFA Cosmetic Ingredient Handbook, Second Edition, 1992.

The fatty alcohols useful herein are those having from about 14 to about 30 carbon atoms, and in another embodiment from about 16 to about 22 carbon atoms. These fatty alcohols are saturated and can be straight or branched chain alcohols. Non-limiting examples of fatty alcohols include, cetyl alcohol, stearyl alcohol, behenyl alcohol, and mixtures thereof.

The fatty acids useful herein are those having from about 10 to about 30 carbon atoms, in one embodiment from about 12 to about 22 carbon atoms, and in another embodiment from about 16 to about 22 carbon atoms. These fatty acids are saturated and can be straight or branched chain acids. Also included are diacids, triacids, and other multiple acids which meet the requirements herein. Also included herein are salts of these fatty acids. Non-limiting examples of fatty acids include lauric acid, palmitic acid, stearic acid, behenic acid, sebacic acid, and mixtures thereof.

The fatty alcohol derivatives and fatty acid derivatives useful herein include alkyl ethers of fatty alcohols, alkoxylated fatty alcohols, alkyl ethers of alkoxylated fatty alcohols, esters of fatty alcohols, fatty acid esters of compounds having esterifiable hydroxy groups, hydroxy-substituted fatty acids, and mixtures thereof. Non-limiting examples of fatty alcohol derivatives and fatty acid derivatives include materials such as methyl stearyl ether; the ceteth series of compounds such as ceteth-1 through ceteth-45, which are ethylene glycol ethers of cetyl alcohol, wherein the numeric designation indicates the number of ethylene glycol moieties present; the steareth series of compounds such as steareth-1 through 10, which are ethylene glycol ethers of steareth alcohol, wherein the numeric designation indicates the number of ethylene glycol moieties present; ceteareth 1 through ceteareth-10, which are the ethylene glycol ethers of ceteareth alcohol, i.e. a mixture of fatty alcohols containing predominantly cetyl and stearyl alcohol, wherein the numeric designation indicates the number of ethylene glycol moieties present; $C_1$-$C_{30}$ alkyl ethers of the ceteth, steareth, and ceteareth compounds just described; polyoxyethylene ethers of behenyl alcohol; ethyl stearate, cetyl stearate, cetyl palmitate, stearyl stearate, myristyl myristate, polyoxyethylene cetyl ether stearate, polyoxyethylene stearyl ether stearate, polyoxyethylene lauryl ether stearate, ethyleneglycol monostearate, polyoxyethylene monostearate, polyoxyethylene distearate, propyleneglycol monostearate, propyleneglycol distearate, trimethylolpropane distearate, sorbitan stearate, polyglyceryl stearate, glyceryl monostearate, glyceryl distearate, glyceryl tristearate, and mixtures thereof.

High melting point fatty compounds of a single compound of high purity are useful herein. Single compounds of pure fatty alcohols can be selected from the group of pure cetyl alcohol, stearyl alcohol, and behenyl alcohol. By "pure" herein, what is meant is that the compound has a purity of at least about 90%, and in another embodiment about 95%. These single compounds of high purity provide good rinsability from the hair when the consumer rinses off the composition.

Commercially available high melting point fatty compounds useful herein include: cetyl alcohol, stearyl alcohol, and behenyl alcohol having trade names KONOL series available from Shin Nihon Rika (Osaka, Japan), and NAA series available from NOF (Tokyo, Japan); pure behenyl alcohol having trade name 1-DOCOSANOL available from WAKO (Osaka, Japan), various fatty acids having trade names NEO-FAT available from Akzo (Chicago Ill., USA), HYSTRENE available from Witco Corp. (Dublin Ohio, USA), and DERMA available from Vevy (Genova, Italy).

The hair conditioning actives of the present invention may also comprise an amidoamine of the following general formula:

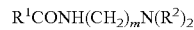

wherein $R^1$ is a residue of $C_{11}$ to $C_{24}$ fatty acids, $R^2$ is a $C_1$ to $C_4$ alkyl, and m is an integer from 1 to 4.

The amidoamine, together with acids, can function as a cationic surfactant in the composition of the present invention. It is believed that; when used in the composition of the present invention, amidoamine can provide improved deposition of silicones especially aminosilicones, compared to other cationic surfactants such as stearyl trimethyl ammonium chloride. It is also believed that; the composition of the present invention can provide improved conditioning benefits such as softness and smoothness due to improved deposition of silicones. It is further believed that; the compositions of the present invention can provide reduced frizziness in addition to softness and smoothness.

Amidoamine useful in the present invention includes stearamidopropyldimethylamine, stearamidopropyldiethylamine, stearamidoethyldiethylamine, stearamidoethyldimethylamine, palmitamidopropyldimethylamine, palmitamidopropyldiethylamine, palmitamidoethyldiethylamine, palmitamidoethyldimethylamine, behenamidopropyldimethylamine, behenamidopropyldiethylamine, behenamidoethyldiethylamine, behenamidoethyldimethylamine, arachidamidopropyldimethylamine, arachidamidopropyldiethylamine, arachidamidoethyldiethylamine, arachidamidoethyldimethylamine, and mixtures thereof; and in another embodiment stearamidopropyldimethylamine, stearamidoethyldiethylamine, and mixtures thereof.

Commercially available amidoamines useful herein include: stearamidopropyldimethylamine having tradename SAPDMA available form Inolex, and tradename Amidoamine MPS available from Nikko, and behenamidopropyl dimethylamine having a tradename IncromineBB available from Croda. Without being limited to the theory, it is believed that behenamidopropyl dimethylamine provides improved tolerance to the hair for humidity in the surrounded circumstance compared to other amidoamines having shorter alkyl chain. It is believed that behenamidopropyl dimethylamine provides reduced frizziness and/or fly-away in rainy day and/or humid day.

The hair conditioning actives of the present invention may comprise an acid selected from the group consisting of L-glutamic acid, lactic acid, hydrochloric acid, malic acid, succinic acid, acetic acid, fumaric acid, L-glutamic acid hydrochloride, tartaric acid, citric acid, and mixtures thereof; in another embodiment L-glutamic acid, lactic acid, citric acid, and mixtures thereof. The mole ratio of amidoamine to acid can be in one embodiment from about 1:0.3 to about 1:1.3, and in another embodiment from about 1:0.5 to about 1:1.0.

The hair conditioning actives of the present invention may comprise one or more silicones including high molecular weight polyalkyl or polyaryl siloxanes and silicone gums; lower molecular weight polydimethyl siloxane fluids; and aminosilicones.

In one embodiment the high molecular weight polyalkyl or polyaryl siloxanes and silicone gums have a viscosity of from about 100,000 mPa·s to about 30,000,000 mPa·s at 25° C. in another embodiment from about 200,000 mPa·s to about 30,000,000 mPa·s and in on embodiment a molecular weight of from about 100,000 to about 1,000,000, and in another embodiment from about 120,000 to about 1,000,000.

Higher molecular weight silicone compounds useful herein include polyalkyl or polyaryl siloxanes with the following structure:

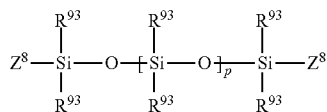

wherein $R^{93}$ is alkyl or aryl, and p is an integer from about 1,300 to about 15,000, and in another embodiment from about 1,600 to about 15,000. $Z^8$ represents groups which block the ends of the silicone chains. The alkyl or aryl groups substituted on the siloxane chain ($R^{93}$) or at the ends of the siloxane chains $Z^8$ can have any structure as long as the resulting silicone remains fluid at room temperature, is dispersible, is neither irritating, toxic nor otherwise harmful when applied to the hair, is compatible with the other components of the composition, is chemically stable under normal use and storage conditions, and is capable of being deposited on and conditions the hair. Suitable $Z^8$ groups include hydroxy, methyl, methoxy, ethoxy, propoxy, and aryloxy. The two $R^{93}$ groups on the silicon atom may represent the same group or different groups. In one embodiment, the two $R^{93}$ groups represent the same group. Suitable $R^{93}$ groups include methyl, ethyl, propyl, phenyl, methylphenyl and phenylmethyl. In one embodiment the silicone compounds are polydimethylsiloxane, polydiethylsiloxane, and polymethylphenylsiloxane. Polydimethylsiloxane, which is also known as dimethicone. Commercially available these silicone compounds useful herein include, for example, those available from the General Electric Company in their TSF451 series, and those available from Dow Corning in their Dow Corning SH200 series.

The silicone compounds that can be used herein also include a silicone gum. The term "silicone gum", as used herein, means a polyorganosiloxane material having a viscosity at 25° C. of greater than or equal to 1,000,000 mPa·s. It is recognized that the silicone gums described herein can also have some overlap with the above-disclosed silicone compounds. This overlap is not intended as a limitation on any of these materials. The "silicone gums" will typically have a mass molecular weight in excess of about 165,000, generally between about 165,000 and about 1,000,000. Specific examples include polydimethylsiloxane, poly(dimethylsiloxane methylvinylsiloxane) copolymer, poly(dimethylsiloxane diphenylsiloxane methylvinylsiloxane) copolymer and mixtures thereof. Commercially available silicone gums useful herein include, for example, TSE200A available from the General Electric Company.

In one embodiment the lower molecular weight silicones have a viscosity of from about 1 mPa·s to about 10,000 mPa·s at 25° C., in another embodiment from about 5 mPa·s to about 5,000 mPa·s and in one embodiment a molecular weight of from about 400 to about 65,000, and in another embodiment from about 800 to about 50,000.

Lower molecular weight silicone compounds useful herein include polyalkyl or polyaryl siloxanes with the following structure:

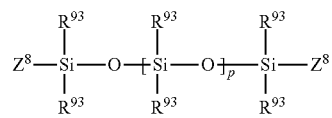

wherein $R^{93}$ is alkyl or aryl, and p is an integer from about 7 to about 850, and in another embodiment from about 7 to about 665. $Z^8$ represents groups which block the ends of the silicone chains. The alkyl or aryl groups substituted on the siloxane chain ($R^{93}$) or at the ends of the siloxane chains $Z^8$ can have any structure as long as the resulting silicone remains fluid at room temperature, is dispersible, is neither irritating, toxic nor otherwise harmful when applied to the hair, is compatible with the other components of the composition, is chemically stable under normal use and storage conditions, and is capable of being deposited on and conditions the hair. Suitable $Z^8$ groups include hydroxy, methyl, methoxy, ethoxy, propoxy, and aryloxy. The two $R^{93}$ groups on the silicon atom may represent the same group or different groups. In one embodiment the two $R^{93}$ groups represent the same group. Suitable $R^{93}$ groups include methyl, ethyl, propyl, phenyl, methylphenyl and phenylmethyl. The silicone compounds useful herein include polydimethylsiloxane, polydiethylsiloxane, and polymethylphenylsiloxane. In one embodiment the silicone is polydimethylsiloxane, which is also known as dimethicone. Commercially available these silicone compounds useful herein include, for example, those available from the General Electric Company in their TSF451 series, and those available from Dow Corning in their Dow Corning SH200 series.

In one embodiment, the active agent of the present invention includes one or more aminosilicones. Aminosilicones, as provided herein, are silicones containing at least one primary amine, secondary amine, tertiary amine, or a quaternary ammonium group. In one embodiment the aminosilicones may have less than about 0.5% nitrogen by weight of the aminosilicone, in another embodiment less than about 0.2%, in yet another embodiment, less than about 0.1%. Higher levels of nitrogen (amine functional groups) in the amino silicone tend to result in less friction reduction, and consequently less conditioning benefit from the aminosilicone. It should be understood that in some product forms, higher levels of nitrogen are acceptable in accordance with the present invention.

In one embodiment, the aminosilicones used in the present invention have a particle size of less than about 50μ once incorporated into the final composition. The particle size measurement is taken from dispersed droplets in the final composition. Particle size may be measured by means of a laser light scattering technique, using a Horiba model LA-910 Laser Scattering Particle Size Distribution Analyzer (Horiba Instruments, Inc.).

In one of the embodiments, the aminosilicone has a viscosity of from about 1,000 cs (centistokes) to about 1,000,000 cs, in another embodiment from about 10,000 cs to about 700,000 cs, in yet another embodiment from about 50,000 cs to about 500,000 cs, and in yet another embodiment from about 100,000 cs to about 400,000 cs. This embodiment may also comprise a low viscosity fluid, such as, for example, those materials described below in Section F.(1). The viscosity of aminosilicones discussed herein is measured at 25° C.

In another embodiment, the aminosilicone has a viscosity of from about 1,000 cs to about 100,000 cs, in another embodiment from about 2,000 cs to about 50,000 cs, in another embodiment from about 4,000 cs to about 40,000 cs, and in yet another embodiment from about 6,000 cs to about 30,000 cs.

The aminosilicone can be contained in the composition of the present invention at a level by weight of from about 0.05% to about 20% in one embodiment, from about 0.1% to about 10% in another embodiment, and from about 0.3% to about 5% in yet another embodiment.

Examples of aminosilicones for use in embodiments of the subject invention include, but are not limited to, those which conform to the general formula (I):

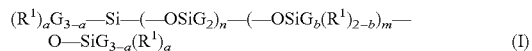

wherein G is hydrogen, phenyl, hydroxy, or $C_1$-$C_8$ alkyl, and in one embodiment methyl; a is 0 or an integer having a value from 1 to 3, and in one embodiment is 1; b is 0, 1, or 2, and in one embodiment is 1; wherein when a is 0, b is not 2; n is a number from 0 to 1,999; m is an integer from 0 to 1,999; the sum of n and m is a number from 1 to 2,000; a and m are not both 0; $R^1$ is a monovalent radical conforming to the general formula $C_qH_{2q}L$, wherein q is an integer having a value from 2 to 8 and L is selected from the following groups: —N($R^2$) $CH_2$—$CH_2$—N($R^2$)$_2$; —N($R^2$)$_2$; —N($R^2$)$^+_3$A$^-$; —N($R^2$) $CH_2$—$CH_2$—N$R^2H_2$A$^-$; wherein $R^2$ is hydrogen, phenyl, benzyl, or a saturated hydrocarbon radical, and in one embodiment is an alkyl radical from about $C_1$ to about $C_{20}$; A$^-$ is a halide ion.

Some silicones for use herein can include those aminosilicones that correspond to formula (I) wherein m=0, a=1, q=3, G=methyl, n is in one embodiment from about 1500 to about 1700, in another embodiment is about 1600; and L is —N($CH_3$)$_2$ or —NH$_2$, and in one embodiment is —NH$_2$. Other aminosilicones can include those corresponding to formula (I) wherein m=0, a=1, q=3, G=methyl, n is in one embodiment from about 400 to about 600, in another embodiment is about 500; and L is —N($CH_3$)$_2$ or —NH$_2$, in yet another embodiment is —NH$_2$. These aminosilicones can be called as terminal aminosilicones, as one or both ends of the silicone chain are terminated by nitrogen containing group.

An exemplary aminosilicone corresponding to formula (I) is the polymer known as "trimethylsilylamodimethicone", which is shown below in formula (II):

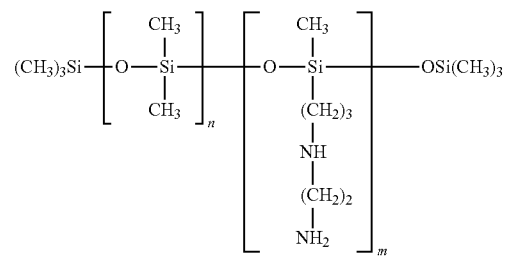

wherein n is a number from 1 to 1,999 and m is a number from 1 to 1,999.

The active agent of the present invention may also include low melting point oils having a melting point of less than 25° C. The low melting point oil useful herein is selected from the group consisting of: hydrocarbon having from 10 to about 40 carbon atoms; unsaturated fatty alcohols having from about 10 to about 30 carbon atoms such as oleyl alcohol; unsaturated fatty acids having from about 10 to about 30 carbon atoms; fatty acid derivatives; fatty alcohol derivatives; ester oils such as pentaerythritol ester oils, trimethylol ester oils, citrate ester oils, and glyceryl ester oils; poly α-olefin oils; and mixtures thereof. Low melting point oils useful herein are selected from the group consisting of: ester oils such as pentaerythritol ester oils, trimethylol ester oils, citrate ester oils, and glyceryl ester oils; poly α-olefin oils; and mixtures thereof, Particularly useful pentaerythritol ester oils and trimethylol ester oils herein include pentaerythritol tetraisostearate, pentaerythritol tetraoleate, trimethylolpropane triisostearate, trimethylolpropane trioleate, and mixtures thereof. Such compounds are available from Kokyo Alcohol with tradenames KAKPTI, KAKTTI, and Shin-nihon Rika with tradenames PTO, ENUJERUBU TP3SO.

Particularly useful citrate ester oils herein include triisocetyl citrate with tradename CITMOL 316 available from Bernel, triisostearyl citrate with tradename PELEMOL TISC available from Phoenix, and trioctyldodecyl citrate with tradename CITMOL 320 available from Bernel.

Particularly useful glyceryl ester oils herein include triisostearin with tradename SUN ESPOL G-318 available from Taiyo Kagaku, triolein with tradename CITHROL GTO available from Croda Surfactants Ltd., trilinolein with tradename EFADERMA-F available from Vevy, or tradename EFA-GLYCERIDES from Brooks.

Particularly useful poly α-olefin oils herein include polydecenes with tradenames PURESYN 6 having a number average molecular weight of about 500 and PURESYN 100 having a number average molecular weight of about 3000 and PURESYN 300 having a number average molecular weight of about 6000 available from Exxon Mobil Co.

Cationic polymers useful herein are those having an average molecular weight of at least about 5,000, typically from about 10,000 to about 10 million, and in one embodiment are from about 100,000 to about 2 million.

Suitable cationic polymers include, for example, copolymers of vinyl monomers having cationic amine or quaternary ammonium functionalities with water soluble spacer monomers such as acrylamide, methacrylamide, alkyl and dialkyl acrylamides, alkyl and dialkyl methacrylamides, alkyl acrylate, alkyl methacrylate, vinyl caprolactone, and vinyl pyrrolidone. Other suitable spacer monomers include vinyl esters, vinyl alcohol (made by hydrolysis of polyvinyl acetate), maleic anhydride, propylene glycol, and ethylene glycol. Other suitable cationic polymers useful herein include, for example, cationic celluloses, cationic starches, cassia and cationic guar gums.

Suitable cationic surfactants include, for example, stearyl trimethyl ammonium chloride, cetyl trimethyl ammonium chloride, behenyl trimethyl ammonium chloride, and distearyl dimethyl ammonium chloride.

Other suitable cationic surfactants can include asymmetric dialkyl quaternized ammonium salt cationic surfactant. The asymmetric dialkyl quaternized ammonium salt cationic surfactant can be included in the composition at a level by weight of in one embodiment from about 0.1% to about 10%, in another embodiment from about 0.2% to about 5%, in yet another embodiment from about 0.4% to about 3% in view of balance between ease-to-rinse feel and wet conditioning benefits. The use of higher level of asymmetric dialkyl quaternized ammonium salt tends to lead to reduced wet conditioning benefits such as reduced slippery feel, while the use of lower level of asymmetric dialkyl quaternized ammonium salt tends to lead to reduced ease-to-rinse feel.

Some of the asymmetric dialkyl quaternized ammonium salt cationic surfactants useful herein are those having the formula (I):

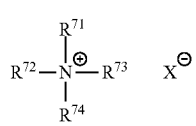

(I)

wherein $R^{71}$ is selected from an alkyl group of from 12 to 30 carbon atoms or an aromatic, alkoxy, polyoxyalkylene, alkylamido, hydroxyalkyl, aryl or alkylaryl group having up to about 30 carbon atoms; $R^{72}$ is selected from an alkyl group of from 5 to 12 carbon atoms or an aromatic, alkoxy, polyoxyalkylene, alkylamido, hydroxyalkyl, aryl or alkylaryl group having up to about 12 carbon atoms; $R^{73}$ and $R^{74}$ are independently selected from an alkyl group of from 1 to about 4 carbon atoms or an aromatic, alkoxy, polyoxyalkylene, alkylamido, hydroxyalkyl, aryl or alkylaryl group having up to about 4 carbon atoms; and $X^-$ is a salt-forming anion such as those selected from halogen, (e.g. chloride, bromide), acetate, citrate, lactate, glycolate, phosphate, nitrate, sulfonate, sulfate, alkylsulfate, and alkyl sulfonate radicals. The alkyl groups can contain, in addition to carbon and hydrogen atoms, ether linkages, and other groups such as amino groups. The longer chain alkyl groups, e.g., those of about 12 carbons, or higher, can be saturated or unsaturated and/or straight or branched. In one embodiment, $R^{71}$ is selected from a non-functionalized alkyl group of from 12 to 30 carbon atoms, in another embodiment from 16 to 22 carbon atoms, in yet another embodiment 18 to 22 carbon atoms, and in yet another embodiment 18 carbon atoms; $R^{72}$ is selected from a non-functionalized alkyl group of in one embodiment from 5 to 12 carbon atoms, in another embodiment from 6 to 10 carbon atoms, in another embodiment 8 carbon atoms; $R^{73}$ and $R^{74}$ are independently selected from $CH_3$, $C_2H_5$, $C_2H_4OH$, and mixtures thereof; and X is selected from the group consisting of Cl, Br, $CH_3OSO_3$, $C_2H_5OSO_3$, and mixtures thereof. In one embodiment, $R^{71}$ is a straight, saturated non-functionalized alkyl group, and $R^{72}$ is a branched saturated non-functionalized alkyl group. In another embodiment, the branched group of $R^{72}$ is a straight, saturated alkyl group of from 1 to 4 carbon atoms, and in yet another embodiment 2 carbon atoms.

The above asymmetric dialkyl quaternized ammonium salt cationic surfactants provide improved ease-to-rinse feel compared to mono-alkyl quaternized ammonium salt cationic surfactants such as behenyl trimethyl ammonium salts and symmetric dialkyl quaternized ammonium cationic surfactants such as distearyl dimethyl ammonium salts, while still maintaining balanced wet conditioning benefits like slippery feel. It has been further found that among the above asymmetric dialkyl quaternized ammonium salt cationic surfactants, those having a longer straight saturated alkyl group and a shorter branched alkyl group, together with two more C1-4 alkyl groups, provide improved balance between ease-to-rinse feel and wet conditioning benefits, compared to other asymmetric dialkyl quaternized ammonium salt cationic surfactants such as those having a longer branched alkyl group and a shorter straight alkyl group together with two more C1-4 alkyl groups. Furthermore, it has been found that; among the above asymmetric dialkyl quaternized ammonium salt cationic surfactants having a longer straight saturated alkyl group and a shorter branched alkyl group, those having the shorter branched alkyl of in one embodiment from 6 to 10 carbon atoms, in another embodiment 8 carbon atoms provide further improved balance between ease-to-rinse feel and wet conditioning benefits, compared to those having the shorter branched alkyl of more than 11 carbon atoms.

It is believed that the use of alkylsulfate such as methosulfate and ethosulfate as a salt-forming anion may be able to provide better conditioning benefits especially wet conditioning benefits, compared to other salt-forming anions.

Nonlimiting examples of asymmetric dialkyl quaternized ammonium salt cationic surfactants useful herein include: stearyl ethylhexyl dimonium methosulfate available, for example, with tradename Arquad HTL8-MS from Akzo Nobel having the following structure:

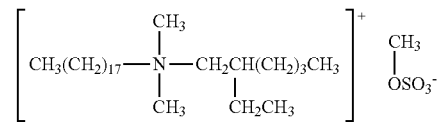

B. Styling Agents

The dissolvable personal care solids of the present invention may comprise an active agent comprising one or more styling agents suitable for application to the hair. Many such styling polymers are known in the art, including dispersible and water-insoluble organic polymers and water-insoluble silicone-grafted polymers. Such polymers can be made by conventional or otherwise known polymerization techniques well known in the art, an example of which includes free radical polymerization. Examples of dispersible polymers are disclosed in, for example, U.S. Pat. No. 5,391,368. Examples of latex polymers are disclosed in, for example, U.S. Pat. No. 4,710,374.

The hair styling polymers suitable for use in the shampoo composition of the present invention include organic hair styling polymers well known in the art. The organic styling polymers may be homopolymers, copolymers, terpolymers or other higher polymers, but must comprise one or more polymerizable hydrophobic monomers to thus render the resulting styling polymer hydrophobic and water-insoluble as defined herein. The styling polymers may therefore further comprise other water soluble, hydrophillic monomers provided that the resulting styling polymers have the requisite hydrophobicity and water insolubility.

As used herein, the term "hydrophobic monomer" refers to polymerizable organic monomers that can form with like monomers a water-insoluble homopolymer, and the term "hydrophilic monomer" refers to polymerizable organic monomers that can form with like monomers a water-soluble homopolymer.

The organic styling polymers useful herein have a weight average molecular weight of at least about 20,000, in one embodiment greater than about 25,000, in another embodiment greater than about 30,000, in yet another embodiment greater than about 35,000. There is no upper limit for molecular weight except that which limits applicability of the invention for practical reasons, such as processing, aesthetic characteristics, formulateability, etc. In general, the weight average molecular weight will be less than about 10,000,000, more generally less than about 5,000,000, and typically less than about 2,000,000. In one embodiment, the weight average molecular weight will be between about 20,000 and about 2,000,000, in another embodiment between about 30,000 and about 1,000,000, and in yet another embodiment between about 40,000 and about 500,000.

The organic styling polymers also in one embodiment have a glass transition temperature (Tg) or crystalline melting point (Tm) of at least about −20° C., in another embodiment from about 20° C. to about 80° C., in yet another embodiment from about 20° C. to about 60° C. Styling polymers having these Tg or Tm values form styling films on hair that are not unduly sticky or tacky to the touch. As used herein, the abbreviation "Tg" refers to the glass transition temperature of the backbone of the polymer, and the abbreviation "Tm" refers to the crystalline melting point of the backbone, if such a transition exists for a given polymer. In one embodiment, both the Tg and the Tm, if any, are within the ranges recited hereinabove.

The organic styling polymers are carbon chains derived from polymerization of hydrophobic monomers such as ethylenically unsaturated monomers, cellulosic chains or other carbohydrate-derived polymeric chains. The backbone may comprise ether groups, ester groups, amide groups, urethanes, combinations thereof, and the like.

The organic styling polymers may further comprise one or more hydrophilic monomers in combination with the hydrophobic monomers described herein, provided that the resulting styling polymer has the requisite hydrophobic character and water-insolubility. Suitable hydrophilic monomers include, but are not limited to, acrylic acid, methacrylic acid, N,N-dimethylacrylamide, dimethyl aminoethyl methacrylate, quaternized dimethylaminoethyl methacrylate, methacrylamide, N-t-butyl acrylamide, maleic acid, maleic anhydride and its half esters, crotonic acid, itaconic acid, acrylamide, acrylate alcohols, hydroxyethyl methacrylate, diallyldimethyl ammonium chloride, vinyl ethers (such as methyl vinyl ether), maleimides, vinyl pyridine, vinyl imidazole, other polar vinyl heterocyclics, styrene sulfonate, allyl alcohol, vinyl alcohol (such as that produced by the hydrolysis of vinyl acetate after polymerization), salts of any acids and amines listed above, and mixtures thereof. Hydrophillic monomers useful herein include acrylic acid, N,N-dimethyl acrylamide, dimethylaminoethyl methacrylate, quaternized dimethyl aminoethyl methacrylate, vinyl pyrrolidone, salts of acids and amines listed above, and combinations thereof.

Suitable hydrophobic monomers for use in the organic styling polymer include, but are not limited to, acrylic or methacrylic acid esters of C1-C18 alcohols, such as methanol, ethanol, methoxy ethanol, 1-propanol, 2-propanol, 1-butanol, 2-methyl-1-propanol, 1-pentanol, 2-pentanol, 3-pentanol, 2-methyl-1-butanol, 1-methyl-1-butanol, 3-methyl-1-butanol, 1-methyl-1-pentanol, 2-methyl-1-pentanol, 3-methyl-1-pentanol, t-butanol(2-methyl-2-propanol), cyclohexanol, neodecanol, 2-ethyl-1-butanol, 3-heptanol, benzyl alcohol, 2-octanol, 6-methyl-1-heptanol, 2-ethyl-1-hexanol, 3,5-dimethyl-1-hexanol, 3,5,5-trimethyl-1-hexanol, 1-decanol, 1-dodecanol, 1-hexadecanol, 1-octa decanol, and the like, the alcohols having in one embodiment from about 1 to about 18 carbon atoms, in another embodiment from about 1 to about 12 carbon atoms; styrene; polystyrene macromer; vinyl acetate; vinyl chloride; vinylidene chloride; vinyl propionate; alpha-methylstyrene; t-butylstyrene; butadiene; cyclohexadiene; ethylene; propylene; vinyl toluene; and mixtures thereof. Hydrophobic monomers useful herein include n-butyl methacrylate, isobutyl methacrylate, t-butyl acrylate, t-butyl methacrylate, 2-ethylhexyl methacrylate, methyl methacrylate, vinyl acetate, and mixtures thereof, in one embodiment t-butyl acrylate, t-butyl methacrylate, or combinations thereof. Surprisingly, it has been found that conventional styling polymers consisting of copolymers of vinyl pyrrolidone and vinyl acetate do not exhibit the curl retention benefits required of the present invention.

The styling polymers for use in the shampoo composition in one embodiment comprise from about 20% to 100%, in another embodiment from about 50% to about 100%, in yet another embodiment from about 60% to about 100%, by weight of the hydrophobic monomers, and may further comprise from zero to about 80% by weight of hydrophilic monomers. The particular selection and combination of monomers for incorporation into the styling polymer will help determine its formulational properties. By appropriate selection and combination of, for example, hydrophilic and hydrophobic monomers, the styling polymer can be optimized for physical and chemical compatibility with the selected styling polymer solvent described hereinafter and other components of the shampoo composition. The selected monomer composition of the organic styling polymer must, however, render the styling polymer water-insoluble but soluble in the selected styling polymer solvent described hereinafter. In this context, the organic styling polymer is soluble in the styling polymer solvent if the organic polymer is solubilized in the solvent at 25° C. at the polymer and solvent concentrations of the shampoo formulation selected. However, a solution of the organic styling polymer and styling polymer solvent may be heated to speed up solubility of the styling polymer in the styling polymer solvent. Such styling polymer and solvent formulation, including the selection of monomers for use in the styling polymer, to achieve the desired solubility is well within the skill of one in the art.

Examples of organic styling polymers useful herein include t-butyl acrylate/2-ethylhexyl acrylate copolymers having a weight/weight ratio of monomers of about 95/5, about 90/10, about 80/20, about 70/30, about 60/40, and about 50/50; t-butyl acrylate/2-ethylhexyl methacrylate copolymers having a weight/weight ratio of monomers of about 95/5, about 90/10, about 80/20, about 70/30, about 60/40, and about 50/50; t-butyl methacrylate/2-ethylhexyl acrylate copolymers having a weight/weight ratio of monomers of about 95/5, about 90/10, about 80/20, about 70/30, about 60/40, and about 50/50; t-butyl methacrylate/2-ethylhexyl methacrylate copolymers having a weight/weight ratio of monomers of about 95/5, about 90/10, about 80/20, about 70/30, about 60/40, and about 50/50; t-butyl ethacrylate/2-ethylhexyl methacrylate copolymers having a weight/weight ratio of monomers of about 95/5, about 90/10, about 80/20, about 70/30, about 60/40, and mixtures thereof.

Polymers useful herein are t-butyl acrylate/2-ethylhexyl methacrylate copolymers having a weight/weight ratio of monomers of about 95/5, about 90/10, about 80/20, about 70/30, about 60/40, and about 50/50; t-butyl methacrylate/2-ethylhexyl methacrylate copolymers having a weight/weight ratio of monomers of about 95/5, about 90/10, about 80/20, about 70/30, about 60/40, and about 50/50; and mixtures thereof.

Examples of other suitable styling polymers are described in U.S. Pat. No. 4,272,511, to Papantoniou et al., issued Jun. 9, 1981; U.S. Pat. No. 5,672,576, to Behrens et al., issued Sep. 30, 1997; and U.S. Pat. No. 4,196,190, to Gehman et al., issued Apr. 1, 1980.

Other suitable styling polymers for use in the shampoo composition of the present invention are silicone-grafted hair styling resins. These polymers may be used alone or in combination with the organic styling polymers described hereinbefore. Many such polymers suitable for use in the shampoo composition herein are known in the art. These polymers are characterized by polysiloxane moieties covalently bonded to and pendant from an uncross-linked polymeric carbon-based backbone.

In one embodiment the backbone of the silicone-grafted polymer is a carbon chain derived from polymerization of ethylenically unsaturated monomers, but can also be cellulosic chains or other carbohydrate-derived polymeric chains to which polysiloxane moieties are pendant. The backbone can also include ether groups, ester groups, amide groups, urethane groups and the like. The polysiloxane moieties can be substituted on the polymer or can be made by co-polymerization of polysiloxane-containing polymerizable monomers (e.g. ethylenically unsaturated monomers, ethers, and/or epoxides) with non-polysiloxane-containing polymerizable monomers. In one embodiment the silicone-grafted styling polymers have a weight average molecular weight of at least about 10,000, in one embodiment greater than about 20,000, in another embodiment greater than about 35,000, in yet another embodiment greater than about 50,000. In one embodiment the weight average molecular weight of the silicone-grafted styling polymer is less than 300,000, in another embodiment less than about 250,000, and in yet another embodiment less than about 150,000.

The silicone-grafted styling polymers for use in the shampoo composition comprise "silicone-containing" (or "polysiloxane-containing") monomers, which form the silicone macromer pendant from the backbone, and non-silicone-containing monomers, which form the organic backbone of the polymer.

In one embodiment the silicone-grafted polymers comprise an organic backbone, in another embodiment a carbon backbone derived from ethylenically unsaturated monomers, such as a vinyl polymeric backbone, and a polysiloxane macromer (in yet another embodiment are polydialkylsiloxane, in another embodiment polydimethylsiloxane) grafted to the backbone. As used hereinafter the term "PDMS" refers to polydimethylsiloxane. In one embodiment the polysiloxane macromer should have a weight average molecular weight of at least about 500, in another embodiment from about 1,000 to about 100,000, in another embodiment from about 2,000 to about 50,000, and in yet another embodiment about 5,000 to about 20,000. Organic backbones contemplated include those that are derived from polymerizable, ethylenically unsaturated monomers, including vinyl monomers, and other condensation monomers (e.g., those that polymerize to form polyamides and polyesters), ring-opening monomers (e.g., ethyl oxazoline and caprolactone), etc. Also contemplated are backbones based on cellulosic chains, ether-containing backbones, etc.

Suitable silicone grafted polymers for use in the shampoo composition comprise monomer units derived from: at least one free radically polymerizable ethylenically unsaturated monomer or monomers and at least one free radically polymerizable polysiloxane-containing ethylenically unsaturated monomer or monomers.

The silicone grafted polymers suitable for use in the shampoo composition generally comprise from about 1% to about 50%, by weight, of polysiloxane-containing monomer units and from about 50% to about 99% by weight, of non-polysiloxane-containing monomers. The non-polysiloxane-containing monomer units can be derived from the hydrophilic and/or hydrophobic monomer units described hereinbefore.

The styling polymer for use in the shampoo composition can therefore comprise combinations of the hydrophobic and/or polysiloxane-containing monomer units described herein, with or without hydrophilic comonomers as described herein, provided that the resulting styling polymer has the requisite characteristics as described herein.

Suitable polymerizable polysiloxane-containing monomers include, but are not limited to, those monomers that conform to the formula:

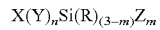

wherein X is an ethylenically unsaturated group copolymerizable with the hydrophobic monomers described herein, such as a vinyl group; Y is a divalent linking group; R is a hydrogen, hydroxyl, lower alkyl (e.g. C1-C4), aryl, alkaryl, alkoxy, or alkylamino; Z is a monovalent siloxane polymeric moiety having a number average molecular weight of at least about 500, which is essentially unreactive under copolymerization conditions, and is pendant from the vinyl polymeric backbone described above; n is 0 or 1; and m is an integer from 1 to 3. These polymerizable polysiloxane-containing monomers have a weight average molecular weight as described above. Examples of such polysiloxane-containing monomers can be found in U.S. Pat. No. 6,177,390B1.

Another polysiloxane monomer conforms to the following formula:

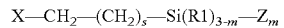

wherein: s is an integer from 0 to about 6, and in one embodiment is 0, 1, or 2; m is an integer from 1 to 3, and in one embodiment is 1; R1 is C1-C10 alkyl or C7-C10 alkylaryl, in another embodiment C1-C6 alkyl or C7-C10 alkylaryl, in yet another embodiment C1-C2 alkyl; and X and Z are as defined above The silicone grafted styling polymers suitable for use in the shampoo composition in one embodiment comprise from about 50% to about 99%, in another embodiment from about 60% to about 98%, in another embodiment from about 75% to about 95%, by weight of the polymer, of non-silicone macromer-containing monomer units, e.g. the total hydrophobic and hydrophilic monomer units described herein, and in one embodiment from about 1% to about 50%, in another embodiment from about 2% to about 40%, in yet another embodiment from about 5% to about 25%, of silicone macromer-containing monomer units, e.g. the polysiloxane-containing monomer units described herein. The level of hydrophilic monomer units can be in one embodiment from about 0% to about 70%, in another embodiment from about 0% to about 50%, in another embodiment from about 0% to about 30%, and in yet another embodiment from about 0% to about 15%; the level of hydrophobic monomer units, can be in one embodiment from 30% to about 99%, in another embodiment from about 50% to about 98%, in another embodiment from about 70% to about 95%, and in yet another embodiment from about 85% to about 95%.

Examples of some suitable silicone grafted polymers for use in the shampoo composition herein are listed below. Each listed polymer is followed by its monomer composition as weight part of monomer used in the synthesis:
(i) t-butylacrylatye/t-butyl-methacrylate/2-ethylhexyl-methacrylate/PDMS macromer-20,000 molecular weight macromer 31/27/32/10
(ii) t-butylmethacrylate/2-ethylhexyl-methacrylate/PDMS macromer-15,000 molecular weight macromer 75/10/15
(iii) t-butylmethacrylate/2-ethylhexyl-acrylate/PDMS macromer-10,000 molecular weight macromer 65/15/20
(iv) t-butylacrylate/2-ethylhexyl-acrylate/PDMS macromer-14,000 molecular weight macromer 77/11/12
(v) t-butylacrylate/2-ethylhexyl-methacrylate/PDMS macromer-13,000 molecular weight macromer 81/9/10

Examples of other suitable silicone grafted polymers for use in the shampoo composition of the present invention are described in EPO Application 90307528.1, published as EPO Application 0 408 311 A2 on Jan. 11, 1991, Hayama, et al.; U.S. Pat. No. 5,061,481, issued Oct. 29, 1991, Suzuki et al.; U.S. Pat. No. 5,106,609, Bolich et al., issued Apr. 21, 1992; U.S. Pat. No. 5,100,658, Bolich et al., issued Mar. 31, 1992; U.S. Pat. No. 5,100,657, Ansher-Jackson, et al., issued Mar. 31, 1992; U.S. Pat. No. 5,104,646, Bolich et al., issued Apr. 14, 1992; U.S. Ser. No. 07/758,319, Bolich et al, filed Aug. 27, 1991, U.S. Ser. No. 07/758,320, Torgerson et al., filed Aug. 27, 1991.

C. Anti-Dandruff Agents (i). Pyrithione or a Polyvalent Metal Salt of Pyrithione The present may comprise pyrithione or a polyvalent metal salt of pyrithione. Any form of polyvalent metal pyrithione salts may be used, including platelet and needle structures. Salts for use herein include those formed from the polyvalent metals magnesium, barium, bismuth, strontium, copper, zinc, cadmium, zirconium and mixtures thereof, and in one embodiment the salt is formed with zinc. In one embodiment the salt is zinc salt of 1-hydroxy-2-pyridinethione (known as "zinc pyrithione" or "ZPT"); ZPT in platelet particle form, wherein the particles have an average size of up to about 20 µm, in one embodiment up to about 5 µm, in another embodiment up to about 2.5 µm.

Pyridinethione anti-microbial and anti-dandruff agents are described, for example, in U.S. Pat. Nos. 2,809,971; 3,236,733; 3,753,196; 3,761,418; 4,345,080; 4,323,683; 4,379,753; and 4,470,982.

Zinc pyrithione may be made by reacting 1-hydroxy-2-pyridinethione (i.e., pyrithione acid) or a soluble salt thereof with a zinc salt (e.g. zinc sulfate) to form a zinc pyrithione precipitate, as illustrated in U.S. Pat. No. 2,809,971.

The pyrithione or polyvalent metal salt of pyrithione can be from about 0.01% to about 5%; and in one embodiment from about 0.1% to about 2%.

In embodiments having a particulate zinc material and a pyrithione or polyvalent metal salt of pyrithione, the ratio of particulate zinc material to pyrithione or a polyvalent metal salt of pyrithione can be from 5:100 to 10:1; and in another embodiment from about 2:10 to 5:1; and in yet another embodiment from 1:2 to 3:1.

(ii). Furametpyr

In one embodiment, the present invention may comprise furametpyr. Furametpyr is a fungicide, and more specifically, furametpyr is in the carboxamide class of anti-fungals. While not being bound by theory, it is generally thought that the furametpyr mechanism is the inhibition of mitochondrial succinate oxidation.

Embodiments of the present invention can include from about 0.01% to about 3% of a furametpyr; in another embodiment from about 0.1% to about 2%; in yet another embodiment from about 0.2% to about 1.5%.

In the present invention, the combination of furametpyr with pyrithione or the polyvalent metal salts of pyrithione may result in an increase in efficacy of a composition. In an embodiment of the present invention, such an increase may be an increase in efficacy for anti-dandruff.

In a further embodiment of the present invention, furametpyr may also be used in combination with other anti-microbial agents. Non-limiting examples of other anti-microbial agents are ketoconazole, climbazole, octopirox, salicylic acid, coal tar, selenium sulfide and mixtures thereof. Such combinations of furametpyr with other anti-microbial agents, may result in an increase in efficacy of a composition, and even more particularly, may increase anti-dandruff efficacy.

Furametpyr generally can be represented by the following formula I:

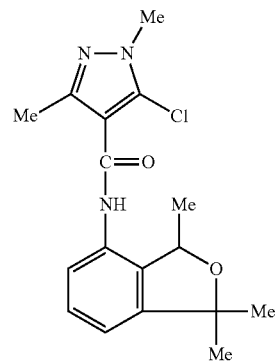

Formula I

Formula: $C_{17}H_{20}Cl\,N_3O_2$
CAS/Registry Number: 123572-88-3
CA Index Name: 1H-Pyrazole-4-carboxamide, 5-chloro-N-(1,3-dihydro-1,1,3-trimethyl-4-isobenzofuranyl)-1,3-dimethyl-(9CI)
Trade Names: Limber®

(iii). Particulate Zinc Material

In a further embodiment of the present invention, the composition of the present invention may include an effective amount of a particulate zinc material. Embodiments of the present invention can include from about 0.001% to about 10% of a particulate zinc layered material; in another embodiment from about 0.01% to about 7%; in yet another embodiment from about 0.1% to about 5%.

Particulate zinc materials (PZM's) are zinc-containing materials which remain mostly insoluble within formulated compositions. Many benefits of PZM's require the zinc ion to be chemically available without being soluble, this is termed zinc lability. Physical properties of the particulate material have the potential to impact lability. We have discovered several factors which impact zinc lability and therefore have led to development of more effective formulas based on PZM's.

Particle physical properties which have been found to be important to optimize zinc lability of PZM's are morphology of the particle, surface area, crystallinity, bulk density, surface charge, refractive index, and purity level and mixtures thereof. Control of these physical properties has been shown to increase product performance.

Examples of particulate zinc materials useful in certain embodiments of the present invention include the following:

Inorganic Materials: Zinc aluminate, Zinc carbonate, Zinc oxide and materials containing zinc oxide (i.e., calamine), Zinc phosphates (i.e., orthophosphate and pyrophosphate), Zinc selenide, Zinc sulfide, Zinc silicates (i.e., ortho- and meta-zinc silicates), Zinc silicofluoride, Zinc Borate, Zinc hydroxide and hydroxy sulfate, zinc-containing layered materials and combinations thereof.

Further, layered structures are those with crystal growth primarily occurring in two dimensions. It is conventional to describe layer structures as not only those in which all the atoms are incorporated in well-defined layers, but also those in which there are ions or molecules between the layers, called gallery ions (A.F. Wells "Structural Inorganic Chemistry" Clarendon Press, 1975). Zinc-containing layered materials (ZLM's) may have zinc incorporated in the layers and/or as more labile components of the gallery ions.

Many ZLM's occur naturally as minerals. Common examples include hydrozincite (zinc carbonate hydroxide), basic zinc carbonate, aurichalcite (zinc copper carbonate hydroxide), rosasite (copper zinc carbonate hydroxide) and many related minerals that are zinc-containing Natural ZLM's can also occur wherein anionic layer species such as clay-type minerals (e.g., phyllosilicates) contain ion-exchanged zinc gallery ions. All of these natural materials can also be obtained synthetically or formed in situ in a composition or during a production process.

Another common class of ZLM's, which are often, but not always, synthetic, is layered doubly hydroxides, which are generally represented by the formula $[M^{2+}_{1-x}M^{3+}_x(OH)_2]^{x+}A^{m-}_{x/m} \cdot nH_2O$ and some or all of the divalent ions ($M^{2+}$) would be represented as zinc ions (Crepaldi, E L, Pava, P C, Tronto, J, Valim, J B *J. Colloid Interfac. Sci.* 2002, 248, 429-42).

Yet another class of ZLM's can be prepared called hydroxy double salts (Morioka, H., Tagaya, H., Karasu, M, Kadokawa, J, Chiba, K *Inorg. Chem.* 1999, 38, 4211-6). Hydroxy double salts can be represented by the general formula $[M^{2+}_{1-x}M^{2+}_{1-x}(OH)_{3(1-y)}]^+A^{n-}_{(1=3y)/n} \cdot nH_2O$ where the two metal ion may be different; if they are the same and represented by zinc, the formula simplifies to $[Zn_{1+x}(OH)_2]^{2x+}2xA^- \cdot nH_2O$. This latter formula represents (where x=0.4) common materials such as zinc hydroxychloride and zinc hydroxynitrate. These are related to hydrozincite as well wherein the divalent anion is replaced by a monovalent anion. These materials can also be formed in situ in a composition or in or during a production process.

These classes of ZLM's represent relatively common examples of the general category and are not intended to be limiting as to the broader scope of materials which fit this definition, including: Natural Zinc containing materials/Ores and Minerals: Sphalerite (zinc blende), Wurtzite, Smithsonite, Franklinite, Zincite, Willemite, Troostite, Hemimorphite and combinations thereof. Organic Salts: Zinc fatty acid salts (i.e., caproate, laurate, oleate, stearate, etc.), Zinc salts of alkyl sulfonic acids, Zinc naphthenate, Zinc tartrate, Zinc tannate, Zinc phytate, Zinc monoglycerolate, Zinc allantoinate, Zinc urate, Zinc amino acid salts (i.e., methionate, phenylalinate, tryptophanate, cysteinate, etc) and combinations thereof. Polymeric Salts: Zinc polycarboxylates (i.e., polyacrylate), Zinc polysulfate and combinations thereof. Physically Adsorbed Forms: Zinc-loaded ion exchange resins, Zinc adsorbed on particle surfaces, Composite particles in which zinc salts are incorporated, (i.e., as core/shell or aggregate morphologies) and combinations thereof. Zinc Salts: zinc oxalate, zinc tannate, zinc tartrate, zinc citrate, zinc oxide, zinc carbonate, zinc hydroxide, zinc oleate, zinc phosphate, zinc silicate, zinc stearate, zinc sulfide, zinc undecylate, and the like, and mixtures thereof; in one embodiment the zinc salt is zinc oxide or zinc carbonate basic.

Commercially available sources of zinc oxide include Z-Cote and Z-Cote HPI (BASF), and USP I and USP II (Zinc Corporation of America).

Commercially available sources of zinc carbonate include Zinc Carbonate Basic (Cater Chemicals: Bensenville, Ill., USA), Zinc Carbonate (Shepherd Chemicals: Norwood, Ohio, USA), Zinc Carbonate (CPS Union Corp.: New York, N.Y., USA), Zinc Carbonate (Elementis Pigments: Durham, UK), and Zinc Carbonate AC (Bruggemann Chemical: Newtown Square, Pa., USA).

Basic zinc carbonate, which also may be referred to commercially as "Zinc Carbonate" or "Zinc Carbonate Basic" or "Zinc Hydroxy Carbonate", is a synthetic version consisting of materials similar to naturally occurring hydrozincite. The idealized stoichiometry is represented by $Zn_5(OH)_6(CO_3)_2$ but the actual stoichiometric ratios can vary slightly and other impurities may be incorporated in the crystal lattice.

Surfactants

The surfactant component of the dissolvable porous solid is essential as a processing aide in preparing a stable solid porous structure for the dissolvable porous solids described herein, although it is understood that the surfactant component should not generate substantial lather during consumer usage for the non-lathering porous solids of the present invention. Accordingly, the surfactant component is employed primarily as a process aid in making a stable foam, wherein the surfactant includes conventional surfactants or emulsifiers that need not provide any lathering performance. Examples of emulsifiers for use as a surfactant component herein include mono- and di-glycerides, fatty alcohols, polyglycerol esters, propylene glycol esters, sorbitan esters and other emulsifiers known or otherwise commonly used to stabilized air interfaces, as for example those used during preparation of aerated foodstuffs such as cakes and other baked goods and confectionary products, or the stabilization of cosmetics such as hair mousses.

(i) Ionic Surfactants

The dissolvable personal care solids of the present invention may comprise a maximum level of 10% (or less than 10%) of ionic surfactants to be used primarily as a process aid in making a stable foam solid, so as to preclude substantial lather formation during consumer usage and dissolution of the porous solid. Ionic surfactants suitable for use in the dissolvable porous solids of the present invention include anionic surfactants, cationic surfactants, zwitterionic surfactants, amphoteric surfactants, or combinations thereof.

Anionic surfactants suitable for use in the personal care compositions of the present invention include those described in McCutcheon's Detergents and Emulsifiers, North American Edition (1986), Allured Publishing Corp.; McCutcheon's, Functional Materials, North American Edition (1992), Allured Publishing Corp.; and U.S. Pat. No. 3,929,678 (Laughlin et al.).

Non-limiting examples of anionic surfactants suitable for use herein include alkyl and alkyl ether sulfates, sulfated monoglycerides, sulfonated olefins, alkyl aryl sulfonates, primary or secondary alkane sulfonates, alkyl sulfosuccinates, acyl taurates, acyl isethionates, alkyl glycerylether sulfonate, sulfonated methyl esters, sulfonated fatty acids, alkyl phosphates, acyl glutamates, acyl sarcosinates, alkyl sulfoacetates, acylated peptides, alkyl ether carboxylates, acyl lactylates, anionic fluorosurfactants, sodium lauroyl glutamate, and combinations thereof.

Anionic surfactants suitable for use in the personal care compositions of the present invention include alkyl and alkyl ether sulfates. These materials have the respective formulae $ROSO_3M$ and $RO(C_2H_4O)_xSO_3M$, wherein R is alkyl or alkenyl of from about 8 to about 24 carbon atoms, x is 1 to 10, and M is a water-soluble cation such as ammonium, sodium, potas-sium and triethanolamine. The alkyl ether sulfates are typically made as condensation products of ethylene oxide and monohydric alcohol's having from about 8 to about 24 carbon atoms. In one embodiment, R has from about 10 to about 18 carbon atoms in both the alkyl and alkyl ether sulfates. The alcohol's can be derived from fats, e.g., coconut oil or tallow, or can be synthetic. Lauryl alcohol and straight chain alcohol's derived from coconut oil are can be useful herein. Such alcohol's are reacted with about 1 to about 10, and in one embodiment 3 to about 5, molar proportions of ethylene oxide and the resulting mixture of molecular species having, for ex-ample, an average of 3 moles of ethylene oxide per mole of alcohol, is sulfated and neutralized.

Specific examples of alkyl ether sulfates which may be used in the personal care compositions are sodium and ammonium salts of coconut alkyl triethylene glycol ether sulfate; tallow alkyl triethylene glycol ether sulfate, and tallow alkyl hexaoxyethylene sulfate. Alkyl ether sulfates useful herein are those comprising a mixture of individual compounds, said mixture having an average alkyl chain length of from about 10 to about 16 carbon atoms and an average degree of ethoxylation of from about 1 to about 4 moles of ethylene oxide.

Other suitable anionic surfactants include water-soluble salts of the organic, sulfuric acid reaction products of the general formula $[R^1—SO_3-M]$, wherein $R^1$ is chosen from the group consisting of a straight or branched chain, saturated aliphatic hydrocarbon radical having from about 8 to about 24, and in one embodiment about 10 to about 18, carbon atoms; and M is a cation. Important examples are the salts of an organic sulfuric acid reaction product of a hydrocarbon of the methane series, including iso-, neo-, ineso-, and n-paraffins, having about 8 to about 24 carbon atoms, and in one embodiment about 10 to about 18 carbon atoms and a sulfonating agent, e.g., $SO_3$, $H_2SO_4$, oleum, obtained according to known sulfonation methods, including bleaching and hydrolysis. Anionic surfactants useful herein include alkali metal and ammonium sulfonated $C_{10-18}$ n-paraffins.

Additional examples of suitable anionic surfactants are the reaction products of fatty acids esterified with isethionic acid and neutralized with sodium hydroxide where, for example, the fatty acids are derived from coconut oil; sodium or potassium salts of fatty acid amides of methyl tauride in which the fatty acids, for example, are derived from coconut oil. Other suitable anionic surfactants of this variety are described in U.S. Pat. Nos. 2,486,921, 2,486,922 and 2,396,278.

Still other suitable anionic surfactants are the succinamates, examples of which include disodium N-octadecylsulfosuccinamate; diammoniumlauryl sulfosuccinamate; tetrasodium N-(1,2-dicarboxyethyl)-N-octadecylsulfosuccinamate; diamyl ester of sodium sulfosuccinic acid; dihexyl ester of sodium sulfosuccinic acid; and dioctyl esters of sodium sulfosuccinic acid.

Other suitable anionic surfactants include olefin sulfonates having about 12 to about 24 carbon atoms. The term "olefin sulfonates" is used herein to mean compounds which can be produced by the sulfonation of a-olefins by means of uncomplexed sulfur trioxide, followed by neutralization of the acid reaction mixture in conditions such that any sulfones which have been formed in the reaction are hydrolyzed to give the corresponding hydroxy-alkanesulfonates. The sulfur trioxide can be liquid or gaseous, and is usually, but not necessarily, diluted by inert diluents, for example by liquid $SO_2$, chlorinated hydrocarbons, etc., when used in the liquid form, or by air, nitrogen, gaseous $SO_2$, etc., when used in the gaseous form.

The α-olefins from which the olefin sulfonates are derived are mono-olefins having about 12 to about 24 carbon atoms, and in one embodiment about 14 to about 16 carbon atoms. In one embodiment, they are straight chain olefins.

In addition to the true alkene sulfonates and a proportion of hydroxy-alkanesulfonates, the olefin sulfonates can contain minor amounts of other materials, such as alkene disulfonates depending upon the reaction conditions, proportion of reactants, the nature of the starting olefins and impurities in the olefin stock and side reactions during the sulfonation process.

Another class of anionic surfactants suitable for use in the personal care compositions are the b-alkyloxy alkane sulfonates. These compounds have the following formula:

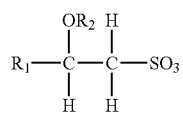

where $R_1$ is a straight chain alkyl group having from about 6 to about 20 carbon atoms, $R_2$ is a lower alkyl group having from about 1 to about 3 carbon atoms, and M is a water-soluble cation as hereinbefore described.

Other suitable surfactants are described in *McCutcheon's, Emulsifiers and Detergents*, 1989 *Annual*, published by M. C. Publishing Co., and in U.S. Pat. No. 3,929,678.

Anionic surfactants for use in the personal care compositions include ammonium lauryl sulfate, ammonium laureth sulfate, triethylamine lauryl sulfate, triethylamine laureth sulfate, triethanolamine lauryl sulfate, triethanolamine laureth sulfate, monoethanolamine lauryl sulfate, monoethanolamine laureth sulfate, diethanolamine lauryl sulfate, diethanolamine laureth sulfate, lauric monoglyceride sodium sulfate, sodium lauryl sulfate, sodium laureth sulfate, potassium lauryl sulfate, potassium laureth sulfate, sodium lauryl sarcosinate, sodium lauroyl sarcosinate, lauryl sarcosine, cocoyl sarcosine, ammonium cocoyl sulfate, ammonium lauroyl sulfate, sodium cocoyl sulfate, sodium lauroyl sulfate, potassium cocoyl sulfate, potassium lauryl sulfate, triethanolamine lauryl sulfate, triethanolamine lauryl sulfate, monoethanolamine cocoyl sulfate, monoethanolamine lauryl sulfate, sodium tridecyl benzene sulfonate, sodium dodecyl benzene sulfonate, and combinations thereof.

Amphoteric surfactants suitable for use in the personal care compositions of the present invention includes those that are broadly described as derivatives of aliphatic secondary and tertiary amines in which the aliphatic radical can be straight or branched chain and wherein one of the aliphatic substituents contains from about 8 to about 18 carbon atoms and one contains an anionic water solubilizing group, e.g., carboxy, sulfonate, sulfate, phosphate, or phosphonate. Examples of compounds falling within this definition are sodium 3-dodecyl-aminopropionate, sodium 3-dodecylaminopropane sulfonate, sodium lauryl sarcosinate, N-alkyltaurines such as the one prepared by reacting dodecylamine with sodium isethionate according to the teaching of U.S. Pat. No. 2,658, 072, N-higher alkyl aspartic acids such as those produced according to the teaching of U.S. Pat. No. 2,438,091, and the products described in U.S. Pat. No. 2,528,378. Zwitterionic surfactants suitable for use include those that are broadly described as derivatives of aliphatic quaternary ammonium, phosphonium, and sulfonium compounds, in which the aliphatic radicals can be straight or branched chain, and wherein one of the aliphatic substituents contains from about 8 to about 18 carbon atoms and one contains an anionic group, e.g., carboxy, sulfonate, sulfate, phosphate, or phosphonate. Zwitterionic surfactants suitable for use in the multiphase, personal care composition include betaines, including cocoamidopropyl betaine.

The amphoteric surfactants of the present invention may also include alkylamphoacetates including lauroamphoacetate and cocoamphoacetate. Alkylamphoacetates can be comprised of monoacetates and diacetates. In some types of alkylamphoacetates, diacetates are impurities or unintended reaction products.

Zwitterionic surfactants suitable for use in the personal care compositions of the present invention include those that are broadly described as derivatives of aliphatic quaternary ammonium, phosphonium, and sulfonium compounds, in which the aliphatic radicals can be straight or branched chain, and wherein one of the aliphatic substituents contains from about 8 to about 18 carbon atoms and one contains an anionic group, e.g., carboxy, sulfonate, sulfate, phosphate, or phosphonate. Such suitable zwitterionic surfactants can be represented by the formula:

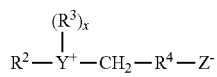

wherein $R^2$ contains an alkyl, alkenyl, or hydroxy alkyl radical of from about 8 to about 18 carbon atoms, from 0 to about 10 ethylene oxide moieties and from 0 to about 1 glyceryl moiety; Y is selected from the group consisting of nitrogen, phosphorus, and sulfur atoms; $R^3$ is an alkyl or monohydroxyalkyl group containing about 1 to about 3 carbon atoms; X is 1 when Y is a sulfur atom, and 2 when Y is a nitrogen or phosphorus atom; $R^4$ is an alkylene or hydroxyalkylene of from about 1 to about 4 carbon atoms and Z is a radical selected from the group consisting of carboxylate, sulfonate, sulfate, phosphonate, and phosphate groups.

Other zwitterionic surfactants suitable for use herein include betaines, including high alkyl betaines such as coco dimethyl carboxymethyl betaine, cocoamidopropyl betaine, cocobetaine, lauryl amidopropyl betaine, oleyl betaine, lauryl dimethyl carboxymethyl betaine, lauryl dimethyl alphacarboxyethyl betaine, cetyl dimethyl carboxymethyl betaine, lauryl bis-(2-hydroxyethyl) carboxymethyl betaine, stearyl bis-(2-hydroxypropyl) carboxymethyl betaine, oleyl dimethyl gamma-carboxypropyl betaine, and lauryl bis-(2-hydroxypropyl)alpha-carboxyethyl betaine. The sulfobetaines may be represented by coco dimethyl sulfopropyl betaine, stearyl dimethyl sulfopropyl betaine, lauryl dimethyl sulfoethyl betaine, lauryl bis-(2-hydroxyethyl) sulfopropyl betaine and the like; amidobetaines and amidosulfobetaines, wherein the $RCONH(CH_2)_3$ radical is attached to the nitrogen atom of the betaine are also useful in this invention.

(ii) Non-Ionic Surfactants

In one embodiment non-ionic surfactants are surfactants to be employed as a process aid in making a the dissolvable porous solids of the present invention. Suitable nonionic surfactants for use in the present invention include those described in McCutcheion's Detergents and Emulsifiers, North American edition (1986), Allured Publishing Corp., and McCutcheion's Functional Materials, North American edition (1992). Suitable nonionic surfactants for use in the personal care compositions of the present invention include, but are not limited to, polyoxyethylenated alkyl phenols, polyoxyethylenated alcohols, polyoxyethylenated polyoxypropylene glycols, glyceryl esters of alkanoic acids, polyglyceryl esters of alkanoic acids, propylene glycol esters of alkanoic acids, sorbitol esters of alkanoic acids, polyoxyethylenated sorbitor esters of alkanoic acids, polyoxyethylene glycol esters of alkanoic acids, polyoxyethylenated alkanoic acids, alkanolamides, N-alkylpyrrolidones, alkyl glycosides, alkyl polyglucosides, alkylamine oxides, and polyoxyethylenated silicones.

Representative polyoxyethylenated alcohols include alkyl chains ranging in the C9-C16 range and having from about 1 to about 110 alkoxy groups including, but not limited to, laureth-3, laureth-23, ceteth-10, steareth-10, steareth-100, beheneth-10, and commercially available from Shell Chemicals, Houston, Tex. under the trade names Neodol® 91, Neodol® 23, Neodol® 25, Neodol® 45, Neodol® 135, Neodol® 67, Neodol® PC 100, Neodol® PC 200, Neodol® PC 600, and mixtures thereof.

Also available commercially are the polyoxyethylene fatty ethers available commercially under the Brij® trade name from Uniqema, Wilmington, Del., including, but not limited to, Brij® 30, Brij® 35, Brij® 52, Brij® 56, Brij® 58, Brij® 72, Brij® 76, Brij® 78, Brij® 93, Brij® 97, Brij® 98, Brij® 721 and mixtures thereof.

Suitable alkyl glycosides and alkyl polyglucosides can be represented by the formula $(S)n$—O—R wherein S is a sugar moiety such as glucose, fructose, mannose, galactose, and the like; n is an integer of from about 1 to about 1000, and R is a C8-C30 alkyl group. Examples of long chain alcohols from which the alkyl group can be derived include decyl alcohol, lauryl alcohol, myristyl alcohol, cetyl alcohol, stearyl alcohol, oleyl alcohol, and the like. Examples of these surfactants include alkyl polyglucosides wherein S is a glucose moiety, R is a C8-20 alkyl group, and n is an integer of from about 1 to about 9. Commercially available examples of these surfactants include decyl polyglucoside and lauryl polyglucoside available under trade names APG® 325 CS, APG® 600 CS and APG® 625 CS) from Cognis, Ambler, Pa. Also useful herein are sucrose ester surfactants such as sucrose cocoate and sucrose laurate and alkyl polyglucosides available under trade names Triton™ BG-10 and Triton™ CG-110 from The Dow Chemical Company, Houston, Tx.

Other nonionic surfactants suitable for use in the present invention are glyceryl esters and polyglyceryl esters, including but not limited to, glyceryl monoesters, glyceryl monoesters of C12-22 saturated, unsaturated and branched chain fatty acids such as glyceryl oleate, glyceryl monostearate, glyceryl monopalmitate, glyceryl monobehenate, and mixtures thereof, and polyglyceryl esters of C12-22 saturated, unsaturated and branched chain fatty acids, such as polyglyceryl-4 isostearate, polyglyceryl-3 oleate, polyglyceryl-2-sesquioleate, triglyceryl diisostearate, diglyceryl monooleate, tetraglyceryl monooleate, and mixtures thereof.

Also useful herein as nonionic surfactants are sorbitan esters. Sorbitan esters of C12-22 saturated, unsaturated, and branched chain fatty acids are useful herein. These sorbitan esters usually comprise mixtures of mono-, di-, tri-, etc. esters. Representative examples of suitable sorbitan esters include sorbitan monolaurate (SPAN® 20), sorbitan monopalmitate (SPAN® 40), sorbitan monostearate (SPAN® 60), sorbitan tristearate (SPAN® 65), sorbitan monooleate (SPAN® 80), sorbitan trioleate (SPAN® 85), and sorbitan isostearate.

Also suitable for use herein are alkoxylated derivatives of sorbitan esters including, but not limited to, polyoxyethylene (20) sorbitan monolaurate (Tween® 20), polyoxyethylene (20) sorbitan monopalmitate (Tween® 40), polyoxyethylene (20) sorbitan monostearate (Tween® 60), polyoxyethylene (20) sorbitan monooleate (Tween® 80), polyoxyethylene (4) sorbitan monolaurate (Tween® 21), polyoxyethylene (4) sorbitan monostearate (Tween® 61), polyoxyethylene (5) sorbitan monooleate (Tween® 81), and mixtures thereof, all available from Uniqema.

Also suitable for use herein are alkylphenol ethoxylates including, but not limited to, nonylphenol ethoxylates (Tergitol™ NP-4, NP-6, NP-7, NP-8, NP-9, NP-10, NP-11, NP-12, NP-13, NP-15, NP-30, NP-40, NP-50, NP-55, NP-70 available from The Dow Chemical Company, Houston, Tx.) and octylphenol ethoxylates (Triton™ X-15, X-35, X-45, X-114, X-100, X-102, X-165, X-305, X-405, X-705 available from The Dow Chemical Company, Houston, Tex).

Also suitable for use herein are alkanolamides including cocamide monoethanolamine (CMEA) and tertiary alkylamine oxides including lauramine oxide and cocamine oxide.

Nonionic surfactants useful herein have an HLB (hydrophile-lipophile balance) of at least 8, in one embodiment greater than 10, and in another embodiment greater than 12. The HLB represents the balance between the hydrophilic and lipophilic moieties in a surfactant molecule and is commonly used as a method of classification. The HLB values for commonly-used surfactants are readily available in the literature (e.g., HLB Index in McCutcheon's Emulsifiers and Detergents, MC Publishing Co., 2004).

(iii) Polymeric Surfactants

Polymeric surfactants can also be surfactants to be employed as a process aid in making the dissolvable porous solids of the present invention, either alone or in combination with ionic and/or nonionic surfactants. Suitable polymeric surfactants for use in the personal care compositions of the present invention include, but are not limited to, block copolymers of ethylene oxide and fatty alkyl residues, block copolymers of ethylene oxide and propylene oxide, hydrophobically modified polyacrylates, hydrophobically modified celluloses, silicone polyethers, silicone copolyol esters, diquaternary polydimethylsiloxanes, and co-modified amino/polyether silicones.

Suitable silicone polyethers, co-modified amino/polyether silicones and silicone copolyol esters may include rake-type copolymers, ABA copolymers, trisiloxane surfactants, and mixtures thereof. Suitable examples include, but are not limited to, polyoxyethylenated dimethicones (KF-607, KF-351, KF-352, KF-353, KF-354L, KF-355A, KF-615A, KF-945, KF-618, KF-6011, KF-6015 from Shin-Etsu, Japan) including PEG-10 Dimethicone (KF-6017 from Shin-Etsu, Japan), polyoxyethylenated and polypropoxylenated dimethicones (Abil EM 90 and Abil EM97 from Evonik, Germany, SF1528 and products available under the Silwet and Silsoft trade names from GE Silicones, New York, and DC 5225C Formulation Aid from Dow Corning, Mich.), co-modified amino/ polyether silicones (X-22-3939A, X-22-3908A from Shin-Etsu, Japan), silicone copolyol esters include, but are not limited to, Dimethicone PEG-7 isostearate (Ultrasil DW18 from Noveon) and Dimethicone PEG-7 olivate (Ultrasil DW-O).

Suitable copolymers of ethylene oxide and fatty alkyl residues include nonionic polyoxyethylene compounds having fatty (hydrophobic) residues at the distill ends of each polyoxyethylene chain including, but not limited to, PEG-150 distearate, PEG-30 Dipolyhydroxystearate (Arlacel P135 from Uniqem), and PEG-12 dipolyhydroxysterate (Arlacel P114).

Suitable diquaternary polydimethylsiloxanes have an average molecular weight in the range from 1000 to 4000, and may contain siloxane chains in the range from 5 to 40 dimethylsiloxy units. Such a diquaternary polydimethylsiloxane is available from Goldschmidt AG, Essen, Germany, as "ABIL-Quat" 3272. "ABIL-Quat" 3270 is another diquaternary polydimethylsiloxane available from Goldschmidt.

Suitable hydrophobically modified polyacrylates are typified by the Pemulen® products and have the INCI name of Acrylates C10-30 Alkyl Acrylates Crosspolymer including, but not limited to Pemulen® TR1.

Suitable hydrophobically modified celluloses include alkyl modified hydroxyethyl cellulose including, but not limited to, Cetyl Hydroxyethyl Cellulose (Natrosol® Plus CS)

Block copolymers of ethylene oxide and propylene oxide include those represented by the following formula: $HO(C_2H_4)_x(C_3H_6O)_y(C_2H_4)_xH$ wherein values of x may range from about 10 to 110 and values y may range, independently of x, from about 20 to 60. Suitable examples are better known as poloxamer block copolymers (124, 188, 237, 338, 407) under the trade name of Pluronic® (L44NF, F68NF, F87NF, F108NF, F127NF) from BASF, Germany.

Water-Soluble Polymer ("Polymer Structurant")

The present invention comprises water-soluble polymer that functions as a structurant. As used herein, the term "water-soluble polymer" is broad enough to include both water-soluble and water-dispersible polymers, and is defined as a polymer with a solubility in water, measured at 25° C., of at least about 0.1 gram/liter (g/L). In some embodiments, the polymers have a solubility in water, measured at 25° C., of from about 0.1 gram/liter (g/L) to about 500 grams/liter (g/L). (This indicates production of a macroscopically isotropic or transparent, colored or colorless solution). The polymers for making these solids may be of synthetic or natural origin and may be modified by means of chemical reactions. They may or may not be film-forming. These polymers should be physiologically acceptable, i.e., they should be compatible with the skin, mucous membranes, the hair and the scalp.

The terms "water-soluble polymer" and "polymer structurant" are used interchangeably herein. Furthermore, whenever the singular term "polymer" is stated, it should be understood that the term is broad enough to include one polymer or a mixture of more than one polymer. For instance, if a mixture of polymers is used, the polymer solubility as referred to herein would refer to the solubility of the mixture of polymers, rather than to the solubility of each polymer individually.

The one or more water-soluble polymers of the present invention are selected such that their weighted average molecular weight is from about 40,000 to about 500,000, in one embodiment from about 50,000 to about 400,000, in yet another embodiment from about 60,000 to about 300,000, and in still another embodiment from about 70,000 to about 200,000. The weighted average molecular weight is computed by summing the average molecular weights of each polymer raw material multiplied by their respective relative weight percentages by weight of the total weight of polymers present within the porous solid.

The water-soluble polymer(s) of the present invention can include, but are not limited to, synthetic polymers including polyvinyl alcohols, polyvinylpyrrolidones, polyalkylene oxides, polyacrylates, caprolactams, polymethacrylates, polymethylmethacrylates, polyacrylamides, polymethylacrylamides, polydimethylacrylamides, polyethylene glycol monomethacrylates, polyurethanes, polycarboxylic acids, polyvinyl acetates, polyesters, polyamides, polyamines, polyethyleneimines, maleic/(acrylate or methacrylate) copolymers, copolymers of methylvinyl ether and of maleic anhydride, copolymers of vinyl acetate and crotonic acid, copolymers of vinylpyrrolidone and of vinyl acetate, copolymers of vinylpyrrolidone and of caprolactam, vinyl pyrollidone/vinyl acetate copolymers, copolymers of anionic, cationic and amphoteric monomers, and combinations thereof.

The water-soluble polymer(s) of the present invention may also be selected from naturally sourced polymers including those of plant origin examples of which include karaya gum, tragacanth gum, gum Arabic, acemannan, konjac mannan, acacia gum, gum ghatti, whey protein isolate, and soy protein isolate; seed extracts including guar gum, locust bean gum, quince seed, and psyllium seed; seaweed extracts such as Carrageenan, alginates, and agar; fruit extracts (pectins); those of microbial origin including xanthan gum, gellan gum, pullulan, hyaluronic acid, chondroitin sulfate, and dextran; and those of animal origin including casein, gelatin, keratin, keratin hydrolysates, sulfonic keratins, albumin, collagen, glutelin, glucagons, gluten, zein, and shellac.

Modified natural polymers are also useful as water-soluble polymer(s) in the present invention. Suitable modified natural polymers include, but are not limited to, cellulose derivatives such as hydroxypropylmethylcellulose, hydroxymethylcellulose, hydroxyethylcellulose, methylcellulose, hydroxypropylcellulose, ethylcellulose, carboxymethylcellulose, cellulose acetate phthalate, nitrocellulose and other cellulose ethers/esters; and guar derivatives such as hydroxypropyl guar.

Water-soluble polymers of the present invention include polyvinyl alcohols, polyvinylpyrrolidones, polyalkylene oxides, starch and starch derivatives, pullulan, gelatin, hydroxypropylmethylcelluloses, methycelluloses, and carboxymethycelluloses.

Water-soluble polymers of the present invention may also include polyvinyl alcohols, and hydroxypropylmethylcelluloses. Suitable polyvinyl alcohols include those available from Celanese Corporation (Dallas, Tex.) under the Celvol trade name including, but not limited to, Celvol 523, Celvol 530, Celvol 540, Celvol 518, Celvol, 513, Celvol 508, Celvol 504, and combinations thereof. Suitable hydroxypropylmethylcelluloses include those available from the Dow Chemical Company (Midland, Mich.) under the Methocel trade name including, but not limited, to Methocel E50, Methocel E15, Methocel E6, Methocel E5, Methocel E3, Methocel F50, Methocel K100, Methocel K3, Methocel A400, and combinations thereof including combinations with above mentioned hydroxypropylmethylcelluloses.

In a particular embodiment, the above mentioned water-soluble polymer(s) of the present invention may be blended with any single starch or combination of starches as a filler material in such an amount as to reduce the overall level of water-soluble polymers required, so long as it helps provide the dissolvable porous solid with the requisite structure and physical/chemical characteristics as described herein. In such instances, the combined weight percentage of the water-soluble polymer(s) and starch-based material generally ranges from about 10% to about 40 wt %, in one embodiment from about 12 to about 30%, and in a particular embodiment from about 15% to about 25% by weight relative to the total weight of the porous solid. The weight ratio of the water-soluble polymer(s) to the starch-based material can generally range from about 1:10 to about 10:1, in one embodiment from about 1:8 to about 8:1, in still another embodiment from about 1:7 to about 7:1, and in yet another embodiment from about 6:1 to about 1:6.

Typical sources for starch-based materials of the present invention can include cereals, tubers, roots, legumes and fruits. Native sources can include corn, pea, potato, banana, barley, wheat, rice, sago, amaranth, tapioca, arrowroot, canna, sorghum, and waxy or high amylase varieties thereof.

The starch-based materials of the present invention may also include native starches that are modified using any modification known in the art, including physically modified starches examples of which include sheared starches or thermally-inhibited starches; chemically modified starches including those which have been cross-linked, acetylated, and organically esterified, hydroxyethylated, and hydroxypropylated, phosphorylated, and inorganically esterified, cationic, anionic, nonionic, amphoteric and zwitterionic, and succinate and substituted succinate derivatives thereof; conversion products derived from any of the starches, including fluidity or thin-boiling starches prepared by oxidation, enzyme conversion, acid hydrolysis, heat or acid dextrinization, thermal and or sheared products may also be useful herein; and pregelatinized starches which are known in the art.

Plasticizer

The porous dissolvable solids of the present invention comprise a water soluble plasticizing agent suitable for use in personal care compositions. Non-limiting examples of suitable plasticizing agents include polyols, copolyols, polycarboxylic acids, polyesters and dimethicone copolyols. Examples of useful polyols include, but are not limited to, glycerin, diglycerin, propylene glycol, ethylene glycol, butylene glycol, pentylene glycol, cyclohexane dimethanol, hexane diol, polyethylene glycol (200-600), sugar alcohols such as sorbitol, manitol, lactitol and other mono- and polyhydric low molecular weight alcohols (e.g., C2-C8 alcohols); mono di- and oligo-saccharides such as fructose, glucose, sucrose, maltose, lactose, and high fructose corn syrup solids and ascorbic acid. Examples of polycarboxylic acids include, but are not limited to citric acid, maleic acid, succinic acid, polyacrylic acid, and polymaleic acid. Examples of suitable polyesters include, but are not limited to, glycerol triacetate, acetylated-monoglyceride, diethyl phthalate, triethyl citrate, tributyl citrate, acetyl triethyl citrate, acetyl tributyl citrate. Examples of suitable dimethicone copolyols include, but are not limited to, PEG-12 dimethicone, PEG/PPG-18/18 dimethicone, and PPG-12 dimethicone. Other suitable plasticizers of the present invention include, but are not limited to, alkyl and allyl phthalates; napthalates; lactates (e.g., sodium, ammonium and potassium salts); sorbeth-30; urea; lactic acid; sodium pyrrolidone carboxylic acid (PCA); sodium hyraluronate or hyaluronic acid; soluble collagen; modified protein; monosodium L-glutamate; alpha & beta hydroxyl acids such as glycolic acid, lactic acid, citric acid, maleic acid and salicylic acid; glyceryl polymethacrylate; polymeric plasticizers such as polyquaterniums; proteins and amino acids such as glutamic acid, aspartic acid, and lysine; hydrogen starch hydrolysates; other low molecular weight esters (e.g., esters of C2-C10 alcohols and acids); and any other water soluble plasticizer known to one skilled in the art of the foods and plastics industries; and mixtures thereof. In one embodiment, the plasticizers include glycerin or propylene glycol and combinations thereof. European Patent Number EP283165B1 discloses other suitable plasticizers, including glycerol derivatives such as propoxylated glycerol.

Optional Ingredients

The porous dissolvable solids of the present invention may further comprise other optional ingredients that are known for use or otherwise useful in personal care compositions, provided that such optional materials are compatible with the selected essential materials described herein, or do not otherwise unduly impair product performance.

Such optional ingredients are most typically those materials approved for use in cosmetics and that are described in reference books such as the CTFA Cosmetic Ingredient Handbook, Second Edition, The Cosmetic, Toiletries, and Fragrance Association, Inc. 1988, 1992. Non limiting examples of such optional ingredients include preservatives, thickeners, sensates, plant extracts, absorbent particles, adhesive particles, hair fixatives, fibers, reactive agents, acids, bases, enzymes, suspending agents, pH modifiers, pigment particles, anti-microbial agents, lotion agents, co-solvents or other additional solvents, and similar other materials.

Other optional ingredients include organic solvents, especially water miscible solvents and co-solvents useful as solublizing agents for polymeric structurants and as drying accelerators. Non-limiting examples of suitable solvents include alcohols, esters, ketones, aromatic hydrocarbons, aliphatic hydrocarbons, ethers, and combinations thereof. In one embodiment the alcohols are monohydric. In another embodiment monohydric alcohols are ethanol, iso-propanol, and n-propanol. In one embodiment esters are ethyl acetate and butyl acetate. Other non-limiting examples of suitable organic solvents are benzyl alcohol, amyl acetate, propyl acetate, acetone, heptane, iso-butyl acetate, iso-propyl acetate, toluene, methyl acetate, iso-butanol, n-amyl alcohol, n-butyl alcohol, hexane, and methyl ethyl ketone. methanol, ethanol, n-propanol, isopropanol, n-butanol, isobutanol, methylethylketone, acetone, and combinations thereof.

Other optional ingredients include latex or emulsion polymers, thickeners such as water soluble polymers, clays, silicas, waxes, ethylene glycol distearate, deposition aids, including coacervate forming components and quaternary amine compounds.

Product Form

The dissolvable porous solids of the present invention can be produced in any of a variety of product forms, including dissolvable porous solids used alone or in combination with other personal care components. The dissolvable porous solids can be continuous or discontinuous when used in the personal care compositions. Regardless of the product form, the key to all of the product form embodiments contemplated within the scope of the method of the present invention is the selected and defined dissolvable porous solid that comprises a combination of a solid polymeric structurant and a surfactant-containing active ingredient, all as defined herein.

The dissolvable porous solids of the present invention are in the form of one or more flat sheets or pads of an adequate size to be able to be handled easily by the user. It may have a square, rectangle or disc shape or any other shape. The pads can also be in the form of a continuous strip including delivered on a tape-like roll dispenser with individual portions dispensed via perforations and or a cutting mechanism. Alternatively, the dissolvable porous solids of the present invention are in the form of one or more cylindrical objects, spherical objects, tubular objects or any other shaped object. The dissolvable porous solids of the present invention can have a thickness (caliper) of from about 0.5 mm to about 10 mm, in one embodiment from about 1 mm to about 7 mm, and in still another embodiment from about 2 mm to about 6 mm. In the case of cylindrical, spherical, or other objects with more of a third dimension versus a pad or strip, the thickness is taken as the maximum distance of the shortest dimension, i.e., the diameter of a sphere or cylinder for instance.

The dissolvable porous solids of the present invention may comprise one or more textured, dimpled or otherwise topographically patterned surfaces including letters, logos or figures. The textured substrate can result from the shape of the substrate, in that the outermost surface of the substrate contains portions that are raised with respect to other areas of the surface. The raised portions can result from the formed shape of the article, for example the article can be formed originally in a dimpled or waffle pattern. The raised portions can also be the result of creping processes, imprinted coatings, embossing patterns, laminating to other layers having raised portions, or the result of the physical form of the dissolvable porous solid substrate itself. The texturing can also be the result of laminating the substrate to a second substrate that is textured.

In a particular embodiment, the dissolvable porous solids of the present invention can be perforated with holes or channels penetrating into or through the porous solid. These perforations can be formed during the drying process via spikes extended from the surface of the underlying mold, belt or other non-stick surface. Alternatively, these perforations can be formed after the drying process via poking or sticking the porous solids with pins, needles or other sharp objects. In one embodiment, these perforations are great in number per surface area, but not so great in number so as to sacrifice the integrity or physical appearance of the porous solid. It has been found that such perforations increase the dissolution rate of the porous solids into water relative to un-perforated porous solids.

The dissolvable porous solids of the present invention can also be delivered via a water insoluble implement or device. For instance, they may be attached or glued by some mechanism to an applicator to facilitate application to hair and/or skin, i.e., a comb, wrag, wand, or any other conceivable water-insoluble applicator. Additionally, the dissolvable porous solids may be adsorbed to the surfaces of a separate high surface area water-insoluble implement, i.e., a porous sponge, a puff, a flat sheet etc. For the latter, the dissolvable porous solid of the present invention may be adsorbed as a thin film or layer or included within a specific regional space provided by the implement.

Product Types

Non-limiting examples of product type embodiments for use by the dissolvable porous solids and methods of the present invention include hair conditioning substrates, moisturizing substrates, other hair treatment substrates, other skin or body treatment substrates, shaving preparation substrates, pet care substrates, personal care substrates containing pharmaceutical or other skin care active, moisturizing substrates, sunscreen substrates, chronic skin benefit agent substrates (e.g., vitamin-containing substrates, alpha-hydroxy acid-containing substrates, etc.), deodorizing substrates, fragrance-containing substrates, and the like.

II. METHOD OF MANUFACTURE

The personal care dissolvable porous solids of the present invention can be prepared by the process comprising: (1)

Preparing a processing mixture comprising surfactant(s), dissolved polymer structurant, plasticizer and other optional ingredients; (2) Aerating the mixture by introducing a gas into the mixture; (3) Forming the aerated wet mixture into a desired one or more shapes; and (4) Drying the aerated wet mixture to a desired final moisture content (e.g., from about 0.5 to 15% moisture, by addition of energy).

Preparation of Processing Mixture

The processing mixture is generally prepared by dissolving the polymer structurant in the presence of water, plasticizer and other optional ingredients by heating followed by optional cooling. This can be accomplished by any suitable heated batch agitation system or via any suitable continuous system involving either single screw or twin screw extrusion or heat exchangers together with either high shear or static mixing. Any process can be envisioned such that the polymer is ultimately dissolved in the presence of water, the surfactant(s), the plasticizer, and other optional ingredients including step-wise processing via pre-mix portions of any combination of ingredients.

The processing mixtures of the present invention comprise: from about 15% to about 50% solids, in one embodiment from about 20% to about 40% solids, and in another embodiment from about 25% to about 35% solids, by weight of the processing mixture before drying; and have a viscosity of from about 2,500 cps to about 35,000 cps, in one embodiment from about 5,000 cps to about 30,000 cps, in another embodiment from about 7,500 cps to about 25,000 cps, and in still another embodiment from about 10,000 cps to about 20,000 cps. The processing mixture viscosity values can be measured on a suitable rheometer, such as a TA Instruments AR500 Rheometer with 4.0 cm diameter parallel plate and 1,200 micron gap at a shear rate of 1.0 reciprocal seconds for a period of 30 seconds at 25° C. (available from TA Instruments, New Castle, Del.), or on a standard viscometer, such as a Brookfield Model DV-1 PRIME Digital Viscometer with CP-41 and CP-42 spindles at a shear rate of 1.0 reciprocal seconds for a period of 2 minutes at 25° C. (available from Brookfield Engineering Laboratories, Inc., Middleboro, Mass.). The % solids content is the summation of the weight percentages by weight of the total processing mixture of all of the solid, semi-solid and liquid components excluding water and any obviously volatile materials such as low boiling alcohols.

Aeration of Processing Mixture

The aeration of the processing mixture is accomplished by introducing a gas into the mixture, in one embodiment by mechanical mixing energy but also may be achieved via other physical or chemical means. The aeration may be accomplished by any suitable mechanical processing means, including but not limited to: (i) Batch tank aeration via mechanical mixing including planetary mixers or other suitable mixing vessels, (ii) semi-continuous or continuous aerators utilized in the food industry (pressurized and non-pressurized), (iii) gas injection, (iv) gas evolution via a pressure drop, or (v) spray-drying the processing mixture in order to form aerated beads or particles that can be compressed such as in a mould with heat in order to form the porous solid.

In a particular embodiment, it has been discovered that the dissolvable porous solids of the present invention can be prepared within semi-continuous and continuous pressurized aerators that are conventionally utilized within the foods industry in the production of marshmallows. Suitable pressurized aerators include the Morton whisk (Morton Machine Co., Motherwell, Scotland), the Oakes continuous automatic mixer (E. T. Oakes Corporation, Hauppauge, N.Y.), the Fedco Continuous Mixer (The Peerless Group, Sidney, Ohio), and the Preswhip (Hosokawa Micron Group, Osaka, Japan).

Forming the Aerated Wet Processing Mixture

The forming of the aerated wet processing mixture may be accomplished by any suitable means to form the mixture in a desired shape or shapes including, but not limited to (i) depositing the aerated mixture to specially designed moulds comprising a non-interacting and non-stick surface including Teflon, metal, HDPE, polycarbonate, neoprene, rubber, LDPE, glass and the like; (ii) depositing the aerated mixture into cavities imprinted in dry granular starch contained in a shallow tray (Starch moulding forming technique widely utilized in the confectionery industry); or (iii) depositing the aerated mixture onto a continuous belt or screen comprising any non-interacting or non-stick material Teflon, metal, HDPE, polycarbonate, neoprene, rubber, LDPE, glass and the like which may be later stamped, cut, embossed or stored on a roll.

Drying the Formed Aerated Wet Processing Mixture

The drying of the formed aerated wet processing mixture may be accomplished by any suitable means including, but not limited to: (i) drying room(s) including rooms with controlled temperature and pressure or atmospheric conditions; (ii) ovens including non-convection or convection ovens with controlled temperature and optionally humidity; (iii) Truck/Tray driers, (iv) multi-stage inline driers; (v) impingement ovens; (vi) rotary ovens/driers; (vii) inline roasters; (viii) rapid high heat transfer ovens and driers; (ix) dual plenum roasters, (x) conveyor driers, (xi) microwave drying technology, and combinations thereof. Any suitable drying means that does not comprise freeze-drying can be used.

Optional ingredients may be imparted during any of the above described four processing steps or even after the drying process.

The dissolvable porous solids of the present invention may also be prepared with chemical foaming agents by in-situ gas formation (via chemical reaction of one or more ingredients, including formation of $CO_2$ by an effervescent system).

III. PERFORMANCE AND PHYSICAL CHARACTERISTICS

Dissolution Rate

The dissolvable porous solid of present invention has a Dissolution Rate that allows the porous solid to rapidly disintegrate during use with the application with water. The Dissolution Rate of the dissolvable porous solid component is determined in accordance with the methodology described below.

Hand Dissolution Method: Approximately 0.5 g of the dissolvable porous solid is placed in the palm of the hand while wearing nitrile gloves. 7.5 $cm^3$ of luke warm tap water (from about 30° C. to about 35° C.) is quickly applied to the product via syringe. Using a circular motion, palms of hands are rubbed together 2 strokes at a time until dissolution occurs (up to 30 strokes). The hand dissolution value is reported as the number of strokes it takes for complete dissolution or as 30 strokes as the maximum (in the case for where the solid is considered non-dissolving).

The dissolvable porous solids of the present invention have a hand dissolution value of from about 1 to about 30 strokes, in one embodiment from about 2 to about 25 strokes, in another embodiment from about 3 to about 20 strokes, and in still another embodiment from about 4 to about 15 strokes.

Thickness

In one embodiment the dissolvable porous solid of present invention is a flat, flexible substrate in the form of a pad, a strip or tape and having a thickness of from about 0.5 mm to about 10 mm, in one embodiment from about 1 mm to about 7 mm, and in another embodiment from about 2 mm to about 6 mm, as measured by the below methodology. In the case of cylindrical, spherical, or other objects with more of a third dimension versus a pad or strip, the thickness is taken as the maximum distance of the shortest dimension, i.e., the diameter of a sphere or cylinder for instance, and the thickness ranges are the same as described above.

The thickness of the dissolvable porous solid (i.e., substrate or sample substrate) is obtained using a micrometer or thickness gage, such as the Mitutoyo Corporation Digital Disk Stand Micrometer Model Number IDS-1012E (Mitutoyo Corporation, 965 Corporate Blvd, Aurora, Ill., USA 60504). The micrometer has a 1 inch diameter platen weighing about 32 grams, which measures thickness at an application pressure of about 40.7 phi (6.32 gm/cm$^2$).

The thickness of the dissolvable porous solid is measured by raising the platen, placing a section of the sample substrate on the stand beneath the platen, carefully lowering the platen to contact the sample substrate, releasing the platen, and measuring the thickness of the sample substrate in millimeters on the digital readout. The sample substrate should be fully extended to all edges of the platen to make sure thickness is measured at the lowest possible surface pressure, except for the case of more rigid substrates which are not flat. For more rigid substrates which are not completely flat, a flat edge of the substrate is measured using only one portion of the platen impinging on the flat portion of the substrate.

Basis Weight

The dissolvable porous solid component of the personal care composition of the present invention has a basis weight of from about 125 grams/m$^2$ to about 3,000 grams/m$^2$, in one embodiment from about 150 grams/m$^2$ to about 1,200 grams/m$^2$, in another embodiment from about 200 grams/m$^2$ to about 1,000 grams/m$^2$, and in still another embodiment from about 300 grams/m$^2$ to about 800 grams/m$^2$.

The Basis Weight of the dissolvable porous solid component of the personal care composition herein is calculated as the weight of the dissolvable porous solid component per area of the selected dissolvable porous solid (grams/m$^2$). The area is calculated as the projected area onto a flat surface perpendicular to the outer edges of the porous solid. For a flat object, the area is thus computed based on the area enclosed within the outer perimeter of the sample. For a spherical object, the area is thus computed based on the average diameter as 3.14×(diameter/2)$^2$. For a cylindrical object, the area is thus computed based on the average diameter and average length as diameter×length. For an irregularly shaped three dimensional object, the area is computed based on the side with the largest outer dimensions projected onto a flat surface oriented perpendicularly to this side. This can be accomplished by carefully tracing the outer dimensions of the object onto a piece of graph paper with a pencil and then computing the area by approximate counting of the squares and multiplying by the known area of the squares or by taking a picture of the traced area (which can be shaded-in for contrast) including a scale and using image analysis techniques.

Density

The dissolvable porous solid of the personal care compositions described herein can be characterized in terms of a density determination.

The density of the dissolvable porous solid is determined by the equation: Calculated Density=Basis Weight of porous solid/(Porous Solid Thickness×1,000), wherein the porous solid has a density of from about 0.03 g/cm$^3$ to about 0.4 g/cm$^3$, in one embodiment from about 0.05 g/cm$^3$ to about 0.3 g/cm$^3$, and in another embodiment from about 0.075 g/cm$^3$ to about 0.2 g/cm$^3$. The Basis Weight and Thickness of the dissolvable porous solid are determined in accordance with the methodologies described herein.

Cell Inter-Connectivity

The dissolvable porous solid personal care products of the present invention with the above mentioned characteristics have a high degree of cell inter-connectivity, i.e., are predominantly open-celled solid foams as opposed to being predominantly closed-cell solid foams. The cell inter-connectivity can be assessed by cutting a 2-3 mm wide sliver of the solid in the z-direction using scissors or a sharp blade, measured across the normal x-y largest surface of the solid, and turning the resulting sliver by 90 degrees to reveal the internal cellular structure of the freshly cut cross-sectional area. This cross-sectional area can be assessed by close visual inspection or, more accurately, by employing magnification under a stereo microscope such as the SZX12 Stereo microscope available from Olympus Olympus America Inc., Center Valley, Pa. The open-celled dissolvable porous solids of the present invention can easily be identified by examining the inner portion of the cross-sectional area which will comprise a predominantly three dimensional network of struts with open void spaces surrounding the struts that are inter-connected to one another including in the third dimension through the depth of the cross-section. In contrast, the inner cross-section of a closed-cell foam will appear as discrete bubbles that are cut across and then only being inter-connected at the cross-sectional surface in two dimensions by virtue of the cutting process employed to generate the exposed cross-sectional area.

Solid Flexibility and Cohesiveness

The physical integrity of the dissolvable porous solids of the present invention (or solid cohesiveness) is assessed via a qualitative rating system by two separate qualitative ratings (1 to 4 scale) on brittleness/flexibility (brittle is breakable) and cohesiveness (ease in removing from molds):

| Brittleness/Flexibility Qualitative Rating | | | |
|---|---|---|---|
| Very brittle = 1 | Somewhat brittle = 2 | Somewhat flexible = 3 | Very flexible = 4 |

| Cohesiveness Qualitative Rating (Ease of removal from molds) | | | |
|---|---|---|---|
| Very difficult = 1 | Somewhat difficult = 2 | Somewhat easy = 3 | Very easy = 4 |

These ratings are assessed on three dimensional molds and resulting flat solids with z-dimension thicknesses between 3 mm and 10 mm and extending in the x-y dimensions encompassing surface areas of between 10 cm$^2$ and 60 cm$^2$ (with any x-y shape including circles, ovals, squares, rectangles etc.). The examples herein were evaluated employing circular Teflon molds and resulting removed solids with 4.15 cm diameters and depths of 0.7 cm. The brittleness/flexibility rating is judged by bending the pad in half and assessing each pad on its propensity for breakage/creasing versus the pads resiliency and ability to return to the original shape. The cohesiveness rating is judged by peeling a freshly dried (after at least 20 hours at 40 degrees Celsius) solid from the mold and noting the difficulty of removal. Solids with low cohesiveness ratings are difficult to remove from the molds in one piece with significant adhesion to the mold surface and with significant solid remaining adhered to the mold after the solid removal process. Solids with high cohesiveness ratings are easy to peel from the molds in one piece and without significant solid remaining adhered to the mold after the solid removal process.

Lather Volume Method

The dissolvable porous solid personal care compositions of the present invention can be considered substantially non-lathering with very low lather volumes, which in one embodiment is from about 0 ml to about 20 ml, in another embodiment is from about 0 ml to about 15 ml, and in yet another embodiment is from about 0 ml to about 10 ml. For perspective, lathering personal care compositions (i.e., shampoos) typically generate lather volumes from about 70 ml to about 110 ml.

The lather volume assessment is performed on 15 g/10" flat Oriental virgin hair switches that have been treated with 0.098 g of artificial liquid sebum [10-22% olive oil, 18-20% coconut 6% dodecane, 1-4% stearic acid, 1-4% cholesterol, 1-4% coconut fatty acid, 18-20% choleth-24]. The hair switch is rinsed with 9-11 grain, 100° F. water at 1.5 gallons/min for 20 seconds with a shower nozzle. For testing the liquid control products, 0.75 cm$^3$ of liquid product are applied to the center of the switch, the lower portion of hair on the switch is then rubbed over the product on the hair 10 times in a circular motion, followed by 40 strokes back and forth (a total of 80 strokes). Lather speed is recorded as the number of strokes when the first lather is obviously generated during the 80 strokes. Lather from operator's gloves is transferred to a graduated cylinder with a 3.5 cm inside diameter and with total capacities of either 70 ml, 110 ml, or 140 ml depending on the total amount of lather generated (height modification of standard sized graduated cylinders via a glass shop). Lather from hair is gathered using one downward stroke on the switch with a tight grip and is also placed into the cylinder. Total lather volume is recorded in milliliters. Three runs per test sample are performed and the mean of the three values is calculated. When testing the dissolvable porous solids of the present invention, 0.20+/−0.01 grams of product are weighed with the aid of scissors if required and applied to the switch and then 2 cm3 of additional water are added to the product via syringe. The lathering technique is then performed as described for liquid products after a 10 second waiting time. If undissolved material remains in hair, it is removed and the weight is determined when dry.

IV. METHODS OF USE

The compositions of the present invention may be used for treating mammalian keratinous tissue such as hair and/or skin, and provide rapid rinse-ability. The method for conditioning the hair may comprise the steps of: a) applying an effective amount of the dissolvable porous solid to the hand, b) wetting the dissolvable porous solid with water and rubbing to dissolve the solid, c) applying the dissolved material to either the hair or skin such as to treat, and d) rinsing the diluted treatment from the hair or skin using water. These steps can be repeated as many times as desired to achieve the desired treatment benefit.

According to yet another embodiment, a method is provided for providing a benefit to mammalian keratinous tissue, comprising the step of applying a composition according to the first embodiment to keratinous tissue in need of regulating.

The present invention provides for a method for regulating the condition of mammalian keratinous tissue, comprising the step of applying one or more compositions described herein to mammalian keratinous tissue in need of regulation.

The amount of the composition applied, the frequency of application and the period of use will vary widely depending upon the purpose of application, the level of components of a given composition and the level of regulation desired. For example, when the composition is applied for whole body or hair treatment, effective amounts generally range from about 0.3 grams to about 10 grams, in one embodiment from about 0.4 grams to about 5 grams, and in yet another embodiment from about 0.5 grams to about 3 grams.

V. Article of Commerce

The present invention provides for an article of commerce comprising one or more compositions described herein, and a communication directing a consumer to dissolve the porous solid and apply the dissolved mixture to keratinous tissue to produce a treatment effect or benefit to keratinous tissue such as skin and/or hair. The communication may be printed material attached directly or indirectly to packaging that contains the composition. Alternatively, the communication may be an electronic or a broadcast message that is associated with the article of manufacture. Alternatively, the communication may describe at least one possible use, capability, distinguishing feature and/or property of the article of manufacture.

VI. EXAMPLES

The following examples further describe and demonstrate embodiments within the scope of the present invention. The examples are given solely for the purpose of illustration and are not to be construed as limitations of the present invention, as many variations thereof are possible without departing from the spirit and scope of the invention. All exemplified amounts are concentrations by weight of the total composition, i.e., wt/wt percentages, unless otherwise specified.

Example 1

Polyvinyl Alcohol and Glycerin Pre-Mix

The following polymer premix compositions were prepared for use during the preparation of the dissolvable porous solids of the present invention:

| Component | 1A | 1B |
| --- | --- | --- |
| Distilled water | 78.0 | 70.7 |
| Glycerin | 2.0 | 7.3 |
| Polyvinyl alcohol[a] | 20.0 | 22.0 |
| Total | 100.0 | 100.0 |

[a]87-89% hydrolyzed, MW 85,000 to 124,000 available from Sigma Aldrich (Catalog Number 363081, batch 09501BE)

Into an appropriately sized and cleaned vessel, the distilled water and glycerin is added with stirring at 100-300 rpm. The polyvinyl alcohol is weighed into a suitable container and slowly added to the main mixture in small increments using a spatula while continuing to stir while avoiding the formation of visible lumps. The mixing speed is adjusted to minimize foam formation. The mixture is slowly heated to 85 C while continuing to stir and then allowed to cool to room temperature. The hazy mixture is allowed to sit overnight resulting in an amber colored clear solution.

Example 2

Retail Liquid Hair Conditioner Product (Pantene Pro-V)

A liquid hair conditioner was purchased for use during the preparation of the dissolvable porous solids of the present invention. The product was Pantene Pro-V Always Smooth Conditioner, 750 ml, which was distributed by Procter and Gamble, Cincinnati, Ohio. The product was purchased in January 2008 with a lot number 71505395BC. The listed ingredients on the bottle were: water, stearyl alcohol, cyclopentasiloxane, cetyl alcohol, stearamidopropyl dimethylamine, glutamic acid, dimethicone, panthenol, panthenyl ethyl ether, benzyl alcohol, fragrance, EDTA, methylchloroisothiazolinone, methylisothiazolinone.

Example 3

Retail Liquid Hair Conditioner Product (Matrix Biolage)

A liquid hair conditioner was purchased for use during the preparation of the dissolvable porous solids of the present invention. The product was Matrix Biolage Detangling Solution, 33.8 Fl. Oz., which was distributed by Matrix LLC, New York, N.Y. The product was purchased in February 2008 with a lot number GC048. The listed ingredients on the bottle were: water, cetearyl alcohol, behentrimonium methosulfate, cetyl alcohol, cyclopentasiloxane, behentrimonium chloride, phenoxyethanol, methylparaben, amodimethicone, fragrance, dimethiconol, stearamine oxide, propylene glycol, C11-15 pareth-7, C12-16 pareth-9, glycerin, trideceth-12, polysorbate 20, citric acid, sunflower extract, bitter almond kernel oil, wheat germ extract, hops extract, ext. violet 2, pollen extract, blue 1.

Example 4

Non-Lathering Fast Dissolving Porous Solid Conditioner

The following dissolving porous solid is prepared in accordance to the present invention:

| Component | Wt % |
| --- | --- |
| Polyvinyl alcohol premix from Example 1 | 40.0 |
| Glycerin | 1.2 |
| Retail Conditioner (Pantene Pro-V) from Example 2 | 51.8 |
| Tween-60[a] | 7.0 |
| Total | 100.0 |

[a]Available from Sigma, catalog number P1629, batch No. 057K0115

The above composition is prepared by mixing via a SpeedMixer™ DAC 400 FV available from FlackTek, Inc., Landrum, S.C. 250 grams of the above components in the given amounts are added into a Max 300 SpeedMixer™ plastic jar with all components being at room temperature. The mixture is thoroughly mixed within the SpeedMixer™ which is run at a rage of approximately 2,750 rounds per minute for a time period of at least 30 seconds. Approximately 20 grams of this mixture is reserved for viscosity measurements. The viscosity of the mixture is approximately 7,000 to 9,000 cps at 1 $s^{-1}$.

The remainder of the above mixture is transferred into a 5 quart stainless steel bowl of a KitchenAid® Mixer Model K5SS (available from Hobart Corporation, Troy, Ohio) and fitted with a flat beater attachment. The mixture is vigorously aerated at high speed for approximately 3 minutes. The resulting aerated mixture is then spread evenly with a spatula into circular Teflon molds (using rubber spatulas straight edge to scrape off excess foam leaving a flat smooth surface level with the top of the mold) with a 4.15 cm diameter and a depth of 0.7 cm which are weighed before and after with average wet mixture weights of 2.6+/−0.04 grams indicating an average wet foam density of approximately 0.28 grams/$cm^3$.

The segregated molds are then placed into a 75 C convection oven for 30 minutes and then placed into a 40 C convection oven for drying overnight. The following day, the molds containing the dried mixture are weighed with subtraction of the original mold weights indicating dry weights of 0.60+/−0.02 grams. The resulting porous solids are removed from the molds with the aid of a thin spatula and tweezers and the thicknesses are measured with a caliper giving 5.0+/−0.4 mm indicating an average resulting dry density of approximately 0.09 grams/$cm^3$ and with an average basis weight of 444 grams per square meter (GSM). The resulting solids are determined (by the methodologies described herein): (i) to be predominantly open-celled; (ii) to exhibit good flexibility with a brittleness/flexibility qualitative rating of 3; (iii) to exhibit good cohesiveness with cohesiveness qualitative rating of 3.5; (iv) to have a rapid dissolution rate with a hand dissolution value of only 3 strokes; (v) to provide good conditioning to hair; and (vi) to be substantially non-lathering with a lather volume of less than 10 ml.

Comparative Example 5

Non-Lathering Slow Dissolving Porous Solid Conditioner

The following dissolving porous solid is not prepared in accordance to the present invention and included for comparative purposes to better demonstrate the important aspects of the present invention:

| Component | Wt % |
| --- | --- |
| Polyvinyl alcohol premix from Example 1 | 60.0 |
| Retail Conditioner (Pantene Pro-V) from Example 2 | 40.0 |
| Total | 100.0 |

The above composition is prepared by mixing via a SpeedMixer™ DAC 400 FV available from FlackTek, Inc., Landrum, S.C. 110 grams of the above components in the given amounts are added into a Max 300 SpeedMixer™ plastic jar with all components being at room temperature. The mixture is thoroughly mixed within the SpeedMixer™ which is run at a rage of approximately 2,750 rounds per minute for a time period of at least 30 seconds. Approximately 8 grams of this mixture is reserved for viscosity measurements. The viscosity of the mixture is approximately 95,000 to 140,000 cps at 1 $s^{-1}$.

The remainder of the above mixture is transferred into a 5 quart stainless steel bowl of a KitchenAid® Mixer Model K5SS (available from Hobart Corporation, Troy, Ohio) and fitted with a flat beater attachment. The mixture is vigorously aerated at high speed for approximately 4 minutes. The resulting aerated mixture is then spread evenly with a spatula into circular Teflon molds (using rubber spatulas straight edge to scrape off excess foam leaving a flat smooth surface level with the top of the mold) with a 4.15 cm diameter and a depth of 0.7 cm which are weighed before and after with average wet mixture weights of 3.3+/−0.06 grams indicating an average wet foam density of approximately 0.35 grams/cm³.

The segregated molds are then placed into a 75 C convection oven for 30 minutes and then placed into a 40 C convection oven for drying overnight. The following day, the resulting porous solids are removed from the molds with the aid of a thin spatula and tweezers and the resulting solids are weighed indicating an average dry weight of 0.69+/−0.08 grams. The thicknesses of the resulting solids are measured with a caliper giving 4.2+/−0 2 mm indicating an average resulting dry density of approximately 0.12 grams/cm³ and with an average basis weight of 510 grams per square meter (GSM). The resulting solids are determined (by the methodologies described herein): (i) to be predominantly closed-celled; (ii) to exhibit poor flexibility with a brittleness/flexibility qualitative rating of 1; (iii) to exhibit poor cohesiveness with cohesiveness qualitative rating of 1.0; (iv) to be non-dissolving with a hand dissolution value of greater than 30 strokes; and (v) to deliver a poor in-use consumer experience (due to poor dissolution resulting in un-dissolvable pieces).

Example 6

Non-Lathering Fast Dissolving Porous Solid Conditioner

The following dissolving porous solid is prepared in accordance with the present invention by dilution of the identical composition of Example 5. The viscosity of the mixture is approximately 95,000 to 140,000 cps at 1 $s^{-1}$.

The viscosity of the mixture is lowered to within the limits of the present invention by dilution with de-ionized water. Approximately 90 grams of de-ionized water are added to the mixture until the resulting viscosity reaches approximately 8,000 to 15,000 cps at 1 $s^{-1}$.

Approximately 100 grams of the reduced viscosity mixture is transferred into a 5 quart stainless steel bowl of a KitchenAid® Mixer Model K5SS (available from Hobart Corporation, Troy, Ohio) and fitted with a flat beater attachment. The mixture is vigorously aerated at high speed for approximately 4 minutes. The resulting aerated mixture is then spread evenly with a spatula into circular Teflon molds (using rubber spatulas straight edge to scrape off excess foam leaving a flat smooth surface level with the top of the mold) with a 4.15 cm diameter and a depth of 0.7 cm which are weighed before and after with average wet mixture weights of 2.3+/−0.03 grams indicating an average wet foam density of approximately 0.24 grams/cm³.

The segregated molds are then placed into a 75 C convection oven for 30 minutes and then placed into a 40 C convection oven for drying overnight. The following day, the molds containing the dried mixture are weighed with subtraction of the original mold weights indicating dry weights of 0.29+/−0.03 grams. The resulting porous solids are removed from the molds with the aid of a thin spatula and tweezers and the thicknesses are measured with a caliper giving 5.7+/−0.4 mm indicating an average resulting dry density of approximately 0.04 grams/cm³ and with an average basis weight of 214 grams per square meter (GSM). The resulting solids are determined (by the methodologies described herein): (i) to be predominantly open-celled; (ii) to exhibit acceptable flexibility with a brittleness/flexibility qualitative rating of 2; (iii) to exhibit acceptable cohesiveness with cohesiveness qualitative rating of 2; (iv) to have a rapid dissolution rate with a hand dissolution value of only 5 strokes; (v) to provide good conditioning to hair; and (vi) to be substantially non-lathering with a lather volume of less than 10 ml.

Comparative Example 7

Non-Lathering Slow Dissolving Porous Solid Conditioner

The following dissolving porous solid is not prepared in accordance to the present invention and included for comparative purposes to better demonstrate the important aspects of the present invention. A mixture composition is prepared with a viscosity greater than Example 6, but less than Comparative Example 5:

| Component | Wt % |
| --- | --- |
| Polyvinyl alcohol premix from Example 1 | 28.0 |
| Retail Conditioner (Pantene Pro-V) from Example 2 | 42.0 |
| De-ionized Water | 30.0 |
| Total | 100.0 |

The above composition is prepared by mixing via a SpeedMixer™ DAC 400 FV available from FlackTek, Inc., Landrum, S.C. 110 grams of the above components in the given amounts are added into a Max 300 SpeedMixer™ plastic jar with all components being at room temperature. The mixture is thoroughly mixed within the SpeedMixer™ which is run at a rage of approximately 2,750 rounds per minute for a time period of at least 30 seconds. Approximately 8 grams of this mixture is reserved for viscosity measurements. The viscosity of the mixture is approximately 30,000 to 35,000 cps at 1 $s^{-1}$.

The remainder of the above mixture is transferred into a 5 quart stainless steel bowl of a KitchenAid® Mixer Model K5SS (available from Hobart Corporation, Troy, Ohio) and fitted with a flat beater attachment. The mixture is vigorously aerated at high speed for approximately 8 minutes. The resulting aerated mixture is then spread evenly with a spatula into circular Teflon molds (using rubber spatulas straight edge to scrape off excess foam leaving a flat smooth surface level with the top of the mold) with a 4.15 cm diameter and a depth of 0.7 cm which are weighed before and after with average wet mixture weights of 3.3+/−0.06 grams indicating an average wet foam density of approximately 0.33 grams/cm³.

The segregated molds are then placed into a 75 C convection oven for 30 minutes and then placed into a 40 C convection oven to dry. After five days, the resulting porous solids are removed from the molds with the aid of a thin spatula and tweezers, but the foams were too crumbly to obtain accurate dry weights and densities. The resulting solids are determined (by the methodologies described herein): (i) to be predominantly closed-celled; (ii) to exhibit poor flexibility with a brittleness/flexibility qualitative rating of 1.0; (iii) to exhibit poor cohesiveness with cohesiveness qualitative rating of 1.0; (iv) to be non-dissolving with a hand dissolution value of greater than 30 strokes; and (v) to deliver a poor in-use consumer experience (due to poor dissolution resulting in un-dissolvable pieces).

Example 8

Non-Lathering Fast Dissolving Porous Solid Conditioner

The following dissolving porous solid is prepared in accordance to the present invention:

| Component | Wt % |
| --- | --- |
| Polyvinyl alcohol premix from Example 1B | 59.9 |
| Glycerin | 1.2 |
| Retail Conditioner (Matrix Biolage) from Example 3 | 18.6 |
| Tween-60[a] | 4.1 |
| Distilled Water | 17.4 |
| Total | 100.0 |

[a]Available from Sigma, catalog number P1629, batch No. 057K0115

The above composition is prepared by mixing via a SpeedMixer™ DAC 400 FV available from FlackTek, Inc., Landrum, S.C. 125 grams of the above components in the given amounts are added into a Max 300 SpeedMixer™ plastic jar with all components being at room temperature. The mixture is thoroughly mixed within the SpeedMixer™ which is run at a rage of approximately 2,750 rounds per minute for a time period of at least 30 seconds. Approximately 8 grams of this mixture is reserved for viscosity measurements. The viscosity of the mixture is approximately 9,500 to 10,500 cps at 1 $s^{-1}$.

Approximately 115 grams of the remainder of the above mixture is transferred into a 5 quart stainless steel bowl of a KitchenAid® Mixer Model K5SS (available from Hobart Corporation, Troy, Ohio) and fitted with a flat beater attachment. The mixture is vigorously aerated at high speed for approximately 5 minutes. The resulting aerated mixture is then spread evenly with a spatula into circular Teflon molds (using rubber spatulas straight edge to scrape off excess foam leaving a flat smooth surface level with the top of the mold) with a 4.15 cm diameter and a depth of 0.7 cm which are weighed before and after with average wet mixture weights of 2.9+/−0.13 grams indicating an average wet foam density of approximately 0.31 grams/cm³.

The segregated molds are then placed into a 40 C convection oven for drying overnight. The following day, the molds containing the dried mixture are weighed with subtraction of the original mold weights indicating dry weights of 0.71+/−0.03 grams. The resulting porous solids are removed from the molds with the aid of a thin spatula and tweezers and the thicknesses are measured with a caliper giving 5.1+/−0.1 mm indicating an average resulting dry density of approximately 0.10 grams/cm³ and with an average basis weight of 525 grams per square meter (GSM). The resulting solids are determined (by the methodologies described herein): (i) to be predominantly open-celled; (ii) to exhibit good flexibility with a brittleness/flexibility qualitative rating of 4.0; (iii) to exhibit good cohesiveness with cohesiveness qualitative rating of 4.0; (iv) to have a rapid dissolution rate with a hand dissolution value of only 8 strokes; (v) to provide good conditioning to hair; and (vi) to be substantially non-lathering with a lather volume of less than 10 ml.

Discussion of Examples

The above representative examples are intended to demonstrate the key aspects of the present invention. Example 4 is in accordance with the present invention and produced from a processing mixture comprising polyvinyl alcohol, a retail conditioner (Pantene Pro-V), a non-ionic surfactant, and a viscosity of between 7,000 to 9,000 cps at 1 $s^{-1}$. Accordingly, Example 4 results in predominantly open-celled porous solids with fast dissolution, good flexibility, good cohesiveness and while being substantially non-lathering. Comparative Example 5 is not in accordance with the present invention and produced from a processing mixture comprising polyvinyl alcohol, a retail conditioner (Pantene Pro-V), but with a significantly higher viscosity of between 95,000 to 140,000 cps at 1 $s^{-1}$. Accordingly, Comparative Example 5 results in predominantly closed-celled porous solids that are non-dissolving as well as having poor flexibility and poor cohesiveness. Example 6 is in accordance with the present invention and produced from the identical starting processing mixture of Example 5, but the processing mixture is diluted with water to enable a significantly lower viscosity of between 8,000 to 15,000 cps at 1 $s^{-1}$. Accordingly, Example 6 results in predominantly open-celled porous solids with fast dissolution as well as acceptable flexibility, acceptable cohesiveness and while being substantially non-lathering. Comparative Example 7 is not in accordance with the present invention and produced from a processing mixture comprising polyvinyl alcohol, a retail conditioner (Pantene Pro-V), but with a viscosity in-between that of Comparative Example 5 and Example 6 of between 30,000 to 35,000 cps at 1 $s^{-1}$. Accordingly, Comparative Example 7 results in predominantly closed-celled porous solids that are non-dissolving as well as having poor flexibility and poor cohesiveness. Example 8 is in accordance with the present invention and produced from a processing mixture comprising polyvinyl alcohol, a retail conditioner (Matrix Biolage), a non-ionic surfactant, and a viscosity of between 9,500 to 10,500 cps at 1 $s^{-1}$. Accordingly, Example 8 results in predominantly open-celled porous solids with fast dissolution, good flexibility, good cohesiveness and while being substantially non-lathering.

Collectively, the above examples demonstrate the discovery that non-lathering rapidly dissolving open-celled porous solids according to the present invention can be produced provided that the processing mixture viscosity is within the desired range (or adjusted otherwise). Importantly, this discovery has surprisingly been found to hold true independent of the polymer mixture components (See Comparative Example 5 relative to Example 6 which have the same composition and only differ via dilution of the original processing mixture) which goes against the conventionally accepted wisdom that it is the polymer type, and specifically the molecular weight, that is the primary driver of porous solid dissolution.

Moreover, the above examples demonstrate the beneficial effect of an added non-ionic surfactant on the structural properties of the fast dissolving open-celled porous solids (flexibility and cohesiveness) while also not sacrificing the intended consumer perception of the solids being non-lathering during usage.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

Every document cited herein, including any cross referenced or related patent or application, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A process for forming a non-lathering personal care article in the form of a porous dissolvable solid structure, wherein said process comprises the steps of:
    (a) preparing a pre-mix comprising a substantially non-lathering surfactant, wherein the non-lathering surfactant is selected from the group consisting of non-ionic surfactant, polymeric surfactant, and mixtures thereof, dissolved polymer structurant, an active selected from the group consisting of a conditioning agent, styling agent, anti-dandruff agent and combinations thereof and a plasticizer, wherein said pre-mix has:
        (i) from about 15% to 40% total solids; and
        (ii) a viscosity of from about 2,500 cps to 30,000 cps;
    (b) aerating said pre-mix by introducing a gas into the pre-mix to form a wet aerated pre-mix;
    (c) forming the wet aerated pre-mix into a desired one or more shapes to form shaped wet pre-mix; and
    (d) drying the shaped wet pre-mix to a desired final moisture content, wherein the final moisture content is from about 0.1% to about 15% moisture, to form the non-lathering personal care article, wherein said non-lathering personal care article has a density of from about 0.06 g/cm$^3$ to about 0.15 g/cm$^3$.

2. The process of claim 1, wherein said water soluble polymer has a weighted average molecular weight of from about 40,000 to about 500,000.

3. The process of claim 1, wherein said process does not comprise a freeze-drying step.

* * * * *